US009200326B2

(12) United States Patent
Hosomi et al.

(10) Patent No.: US 9,200,326 B2
(45) Date of Patent: Dec. 1, 2015

(54) PROBE FOR DETECTING POLYMORPHISM IN DISEASE-RELATED GENE AND USE OF THE PROBE

(75) Inventors: Toshiya Hosomi, Kyoto (JP); Mariko Komori, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 13/514,315

(22) PCT Filed: Dec. 7, 2010

(86) PCT No.: PCT/JP2010/071918
§ 371 (c)(1),
(2), (4) Date: Jun. 7, 2012

(87) PCT Pub. No.: WO2011/071046
PCT Pub. Date: Jun. 16, 2011

(65) Prior Publication Data
US 2012/0244540 A1  Sep. 27, 2012

(30) Foreign Application Priority Data

Dec. 7, 2009 (JP) ................................. 2009-278061

(51) Int. Cl.
C12Q 1/68 (2006.01)
C12P 19/34 (2006.01)
C07H 21/02 (2006.01)
C07H 21/04 (2006.01)

(52) U.S. Cl.
CPC ........ *C12Q 1/6886* (2013.01); *C12Q 2600/106* (2013.01)

(58) Field of Classification Search
None
See application file for complete search history.

(56) References Cited

U.S. PATENT DOCUMENTS

| | | | |
|---|---|---|---|
| 4,889,818 A | | 12/1989 | Gelfand et al. |
| 5,079,352 A | | 1/1992 | Gelfand et al. |
| 5,876,930 A | * | 3/1999 | Livak et al. ................. 435/6.11 |
| 6,268,136 B1 | * | 7/2001 | Shuber et al. ................ 435/6.14 |
| 6,582,908 B2 | * | 6/2003 | Fodor et al. ........................ 506/9 |
| 6,773,882 B2 | * | 8/2004 | Hogan et al. ................. 435/6.15 |
| 7,081,336 B2 | * | 7/2006 | Bao et al. ..................... 435/6.11 |
| 2003/0022177 A1 | * | 1/2003 | Wittwer et al. .................... 435/6 |
| 2004/0121348 A1 | | 6/2004 | Kreutzer et al. |
| 2008/0176226 A1 | | 7/2008 | Chiou et al. |
| 2009/0113980 A1 | | 5/2009 | Hirai et al. |
| 2011/0244460 A1 | | 10/2011 | Hirai et al. |
| 2013/0123342 A1 | * | 5/2013 | Brown ......................... 514/44 A |

FOREIGN PATENT DOCUMENTS

| | | |
|---|---|---|
| EP | 0455430 A2 | 11/1991 |
| JP | 2005-506385 A | 3/2005 |
| WO | 91/09950 A1 | 7/1991 |
| WO | 92/09689 A1 | 6/1992 |
| WO | 03/035870 A1 | 5/2003 |
| WO | 2008/084672 A1 | 7/2008 |
| WO | 2010/071147 A1 | 6/2010 |

OTHER PUBLICATIONS

Diffenbach (PCR methods and Applications (1993) vol. 3, pp. S30-S37).*
Roux et al (PCR Methods and Applications (1995) vol. 4, pp. s185-s194).*
Chen et al., "Rapid Detection of K-ras Mutations in Bile by Peptide Nucleic Acid-mediated PCR Clamping and Melting Curve Analysis: Comparison with Restriction Fragment Length Polymorphism Analysis," Clinical Chemistry: 50: 481-489 (2004).
Akiyoshi et al., "Analysis of KRAS gene mutation in advanced/recurrent colon cancer using high resolution melting curve analysis (HRMA)," The Journal of Japan Society for Cancer Therapy, 44: 448 (2009), partial translation.
Benlloch et al., "Detection of BRAF V600E Mutation in Colorectal Cancer," Journal of Molecular Diagnostics, 8: 540-543 (2006).
Liu et al., "Lack of BRAF Activating Mutations in Prostate Adenocarcinoma," Applied Immunohistochemistry & Molecular Morphology, 17: 121-125 (2009).
Luo et al., "Detection of rare mutant K-ras DNA in a single-tube reaction using peptide nucleic acid as both PCR clamp and sensor probe," Nucleic Acids Research, 34: e12 (2006).
Mori et al., "Rapid and Hi-resolution Detection of K-ras Alterations using PCR with Melting Curve Analysis in Body Fluid Specimens," Japanese Journal of Clinical Laboratory. Automation, 31: 270-275 (2006), abstract only.
Samowitz et al., "Relationship of Ki-ras Mutations in Colon Cancers to Tumor Location, Stage, and Survival: A Population-based Study," Cancer Epidemiology, Biomarkers & Prevention, 9: 1193-1197 (2000).
Sato et al., "Detection of a K-ras point mutation employing peptide nucleic acid at the surface of a SPR biosensor," Colloids and Surfaces B. Biointerfaces, 27: 23-31 (2003).
Siena et al., "Biomarkers Predicting Clinical Outcome of Epidermal Growth Factor Receptor-Targeted Therapy in Metastatic Colorectal Cancer," Journal of the National Cancer Institute, 101: 1308-1324 (2009).
Willmore-Payne et al., "BRAF and c-kit gene copy number in mutation-positive malignant melanoma," Human Pathology, 37: 520-527(2006).
Yoshinaga et al., "Development in method of searching for KRAS mutation in colon cancer with high sensitivity," The Japanese Journal of Gastroenterological Surgery, 42: 982 (2009), partial translation.
Extended European Search Report issued in corresponding European Patent Application No. 10835966.2 dated Jun. 10, 2013.
Mod et al., "Rapid, Simple, and Accurate Detection of K-ras Mutations From Body Fluids Using Real-Time PCR and DNA Melting Curve Analysis," Laboratory Medicine, 37: 286-289 (2006).

(Continued)

*Primary Examiner* — Katherine Salmon

(74) *Attorney, Agent, or Firm* — Morgan, Lewis & Bockius LLP

(57) ABSTRACT

The present invention provides a polymorphism detection probe that can identify a different polymorphism in a K-ras gene easily with high reliability and use of the polymorphism detection probe.

28 Claims, 15 Drawing Sheets

(56) References Cited

OTHER PUBLICATIONS

Nakao et al., "Rapid and reliable detection of N-ras mutations in acute lymphoblastic leukemia by melting curve analysis using LightCycler technology," Leukemia, 14:312-315 (2000).

Whitehall et al., "A Multicenter Blinded Study to Evaluate KRAS Mutation Testing Methodologies in the Clinical Setting," Journal of Molecular Diagnostics, 11:543-552 (2009).
Office Action issued in counterpart European Patent Application No. 10835966.2 dated Apr. 2, 2014.

* cited by examiner

PROBE FOR DETECTING POLYMORPHISM IN DISEASE-RELATED GENE AND USE OF THE PROBE

CROSS-REFERENCE TO RELATED APPLICATION

The present application is a U.S. National Phase Application of International Application No. PCT/JP2010/071918, filed Dec. 7, 2010, which claims the benefit of Japanese Patent Application No. 2009-278061, filed Dec. 7, 2009, both of which are hereby incorporated by reference in their entirety.

SEQUENCE LISTING SUBMISSION VIA EFS-WEB

A computer readable text file, entitled "SequenceListing.txt," created on or about Apr. 25, 2012 with a file size of about 9 kb contains the sequence listing for this application and is hereby incorporated by reference in its entirety.

TECHNICAL FIELD

The present invention relates to a probe for detecting a polymorphism in a disease-related gene and use of the probe.

BACKGROUND ART

Each of an RAS protein and an RAF protein is a protein that forms a cascade of intracellular signaling in an RAS/RAF/MAPK pathway. In the RAS/RAF/MAPK pathway, the RAF protein is activated by an activated RAS protein, an MEK protein is activated by the activated RAF protein, and further, an MAPK protein is activated by the activated MEK protein. By this activation, cell growth and cell differentiation are controlled.

A K-ras protein that is a kind of the RAS protein is a GDP/GTP binding protein having GTPase activity. In human, the K-ras protein is encoded by a K-ras gene located on chromosome 12. It is known that the K-ras gene has a mutation in codons 12 to 13 and the like thereof (Non-Patent Documents 1-3). The mutation in the codon 12 is, in a partial sequence of SEQ ID NO: 1 in the K-ras gene, a substitution of adenine (a), cytosine (c), or thymine (t) for guanine (g) at the 220th nucleotide (n) or a substitution of adenine (a), cytosine (c), or thymine (t) for guanine (g) at the 221st nucleotide (n). The mutation in the codon 13 is, in the nucleotide sequence of SEQ ID NO: 1 in the K-ras gene, a substitution of thymine (t) for guanine (g) at the 223rd nucleotide (k) or a substitution of adenine (a) for guanine (g) at the 224th nucleotide (r). By the mutation in the codon 12, glycine (G) at the 12nd position of the K-ras protein is mutated to serine (S), arginine (R), cysteine (C), aspartic acid (D), alanine (A), valine (V), asparagine (N), phenylalanine (F), or leucine (L). By the mutation in the codon 13, glycine (G) at the 13rd position of the K-ras protein is mutated to aspartic acid (D) or cysteine (C). It has been reported that the mutation in codon 12 or 13 of the K-ras gene has connections with, for example, cancer diseases such as colonic cancer and pancreatic cancer, congenital diseases such as CFC (cardio-facio-cutaneous) and the like, and the drug resistance to an anti-EGFR antibody drug (Non-Patent Documents 1-3). Therefore, the detection of the presence or absence of these mutations in the K-ras gene, i.e., the detection of polymorphisms in the K-ras gene is very important in, for example, diagnoses of the above-mentioned diseases, selections of more effective treatment methods for the diseases, and the like.

Moreover, a BRAF protein that is a kind of the RAF protein is a protein having serine-threonine kinase activity. In human, the BRAF protein is encoded by the BRAF gene located on the chromosome 7. It has also been reported that, as well as the mutation in the K-ras gene, a mutation in the BRAF gene has connections with the above-mentioned cancer diseases, congenital diseases, and drug resistance (Non-Patent Documents 1-3). As the mutation in the BRAF gene, a substitution of adenine (a) for thymine (t) at the 229th nucleotide (w) in a partial sequence of SEQ ID NO: 2 in the BRAF gene is known. When the nucleotide is of a wild-type (t), the 600th amino acid in the BRAF protein becomes valine (V). When the nucleotide is of a mutant-type (a), the 600th amino acid in the BRAF protein becomes glutamic acid (E). It is considered that tumorigenicity is obtained by the mutation of this amino-acid residue. Therefore, the detection of the presence or absence of the mutation in the BRAF gene, i.e., the detection of a polymorphism in the BRAF gene besides the mutation in the K-ras gene makes it possible to further improve accuracy of, for example, diagnoses of the above-mentioned diseases, selections of more effective treatment methods for the diseases, and the like.

On the other hand, as a method for detecting a polymorphism in a gene, various methods have been reported. Examples thereof include a PCR (Polymerase Chain Reaction)-RFLP (Restriction Fragment Length Polymorphism) method and the like.

The PCR-RFLP method is carried out by amplifying a detection target region in a target DNA in a sample by PCR, treating the obtained amplification product with a restriction enzyme, and typing the change in restriction fragment length caused by a polymorphism according to Southern hybridization. When a target mutation is present in the gene, the recognition site of the restriction enzyme disappears. Thus, it is possible to detect the presence or absence of the mutation based on the presence or absence of cleavage, i.e., the change in restriction fragment length.

However, in the PCR-RFLP method, for example, after the PCR, it is necessary to conduct a cumbersome procedure of treating the obtained amplification product with a restriction enzyme and conducting an analysis. Furthermore, in order to treat the obtained amplification product with a restriction enzyme, the amplification product has to be temporarily taken out. Thus, there is a risk that the amplification product obtained in a first reaction may scatter and be mixed in a second reaction that is different from the first reaction. Such problems make the automation of the polymorphism detection difficult.

In light of these problems, Tm (Melting Temperature) analysis is attracting attention as a method for detecting a polymorphism in recent years. In the Tm analysis, first, using a probe complementary to a region including a detection target polymorphism, a hybrid (double-stranded nucleic acid) of a nucleic acid to be examined (hereinafter simply referred to as a "test nucleic acid") with the probe is formed. Then, the thus-obtained hybrid is heat-treated, and dissociation (melting) of the hybrid into single-stranded nucleic acids accompanying the temperature rise is detected by measuring signals such as absorbances. By determining the Tm value based on the result of the detection, the polymorphism is determined. The Tm value becomes higher as the complementarity between the single-stranded nucleic acids of the hybrid becomes higher, and becomes lower as the complementarity between the same becomes lower. Thus, in the case where the polymorphism in a detection target site is X or Y, the Tm value of a hybrid composed of a nucleic acid containing the target polymorphism (e.g., Y) and a probe that is 100% complementary thereto is determined beforehand (the Tm value as an evaluation standard value). Subsequently, the Tm value of a hybrid composed of the test nucleic acid and the probe is measured (the Tm value as a measured value). Then, when this measured value is the same as the evaluation standard value, it can be determined that the test nucleic acid shows a perfect match with the probe, i.e., the detection target site in the test nucleic acid is the target polymorphism (Y). On the other hand, when the measured value is lower than the evaluation standard value, it can be determined that the test nucleic acid shows a mismatch with the probe, i.e., the detection target site in the test nucleic acid is the other polymorphism (X). According to such a method, a polymorphism can be detected merely by thermal-treating a PCR reaction solution containing the probe and then measuring signals, for example. Thus, it is possible to automate a detecting device.

However, in detection methods utilizing such Tm analysis, it is necessary to determine the difference in a single nucleotide from the Tm value, for example. Further, in the case where a gene has a plurality of polymorphisms, since analysis of even one sample is accompanied by a considerable amount of work, there is a problem in that the analysis of many samples is impractical. Therefore, in particular, even in the case where a wild-type polymorphism and a plurality of mutant-type polymorphisms are present together, it is required to detect the presence or absence of mutation accurately.

PRIOR ART DOCUMENTS

Non-Patent Documents

[Non-Patent Document 1] Cancer Epidemiology Biomarkers, November, 2000, pp. 1193-1197
[Non-Patent Document 2] J Mol Diagn., November, 2006, Vol. 8, No. 5, pp. 540-543
[Not-Patent Document 3] J Natl Cancer Inst., Oct. 7, 2009, Vol. 101, No. 19, pp. 1308-1324 (Epub: Sep. 8, 2009)

SUMMARY OF INVENTION

Problem to be Solved by the Invention

For the above-described reasons, the detection of a polymorphism in the K-ras gene is very important in, for example, diagnoses of the above-described diseases and selections of the treatment methods for the diseases. Hence, the present invention is intended to provide a probe that can identify a polymorphism in a K-ras gene that is a disease-related gene easily with high reliability, and use of the probe.

Means for Solving Problem

In order to achieve the aforementioned object, the present invention provides a probe for detecting a polymorphism in a K-ras gene that is a disease-related gene, including at least one of oligonucleotides (P1), (P2), (P3), (P1'), (P2'), and (P3'):

(P1) a 11- to 50-mer oligonucleotide that is composed of a nucleotide sequence complementary to a nucleotide sequence including 220th to 230th nucleotides in SEQ ID NO: 1 and has a nucleotide complementary to the 230th nucleotide in its 5' end region;

(P1') an oligonucleotide composed of a nucleotide sequence complementary to the oligonucleotide (P1);

(P2) a 15- to 50-mer oligonucleotide that is composed of a nucleotide sequence complementary to a nucleotide sequence including 220th to 234th nucleotides in SEQ ID NO: 1 and has a nucleotide complementary to the 234th nucleotide in its 5' end region;

(P2') an oligonucleotide composed of a nucleotide sequence complementary to the oligonucleotide (P2);

(P3) 17- to 50-mer oligonucleotide that is composed of a nucleotide sequence complementary to a nucleotide sequence including 220th to 236th nucleotides in SEQ ID NO: 1 and has a nucleotide complementary to the 236th nucleotide in its 5' end region; and (P3') an oligonucleotide composed of a nucleotide sequence complementary to the oligonucleotide (P3).

The present invention also provides a regent for detecting a polymorphism in a disease-related gene, containing the probe of the present invention.

The present invention also provides a method for detecting a polymorphism in a K-ras gene that is a disease-related gene, the method comprising the step of: detecting a polymorphism in a K-ras gene that is a disease-related gene using the probe of the present invention.

Effects of the Invention

According to the probe of the present invention, a polymorphism in a K-ras gene may be identified easily with high reliability by Tm analysis, for example. Specifically, for example, even in the case where a K-ras gene having a wild-type target polymorphism and a K-ras gene having a mutant-type target polymorphism are present together in a sample, the type of polymorphism or the presence or absence of mutation may be detected easily with high reliability by the Tm analysis using the probe of the present invention. Therefore, the present invention is particularly useful when applied to a sample containing both the wild-type K-ras gene and the mutant-type K-ras gene. As described above, according to the present invention, a polymorphism in a K-ras gene can be identified easily with high reliability, so that, for example, the detection result can be reflected in diagnoses of the above-mentioned diseases and selections of treatment methods for the diseases. Therefore, it can be said that the present invention is very useful in a medical field and the like.

DESCRIPTION OF EMBODIMENTS

Figure 1A:
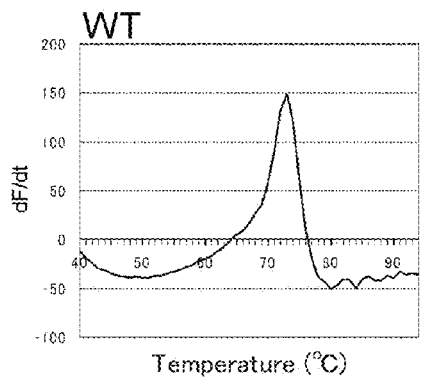
FIGS. 1A to 1E are graphs illustrating the results of Tm analysis with respect to the respective reaction solutions, each containing a wild-type oligonucleotide and a mutant-type oligonucleotide in Example 1 of the present invention.

In the present invention, a detection target polymorphism in the K-ras gene is a polymorphism in codons 12 to 13 of the K-ras gene. Specifically, for example, the detection target polymorphism may be a polymorphism in the codon 12 from the 220th to 222nd nucleotides (nnt) and a polymorphism in the codon 13 from the 223rd to 225th nucleotides (krc) in a partial sequence of SEQ ID NO: 1 in the K-ras gene. The n is g, c, t, or a. The k is g or t. The r is g or a. Codon 12 having a wild-type polymorphism is represented by ggt. Codon 12 having a mutant-type polymorphism can be represented by any of nine types of agt, cgt, tgt, gat, gct, gtt, aat, ttt, and ctt, for example. Codon 13 having a wild-type polymorphism is represented by ggc. Codon 13 having a mutant-type polymorphism can be represented by any of gac and tgc, for example. When at least one of the polymorphism in codon 12 and the polymorphism in codon 13 of the K-ras gene is of a mutant-type, for example, it can be determined that the resistance against an anti-EGFR antibody drug such as cetuximab is exerted. When it is of a wild-type, for example, it can be determined that the resistance is not exerted. As the polymorphisms in codons 12 to 13 from the 220th to 225th nucleotides in a sense strand of the K-ras gene, a wild-type 1 and mutant-types 2-13 are shown below as examples. In the following sequences, underlined nucleotides are mutant-type nucleotides.

| Wild-type | 1 | (WT) | | ggtggc |
|---|---|---|---|---|
| Mutant-type | 2 | (c12-AGT) | | agtggc |
| | 3 | (c12-CGT) | | cgtggc |
| | 4 | (c12-TGT) | | tgtggc |
| | 5 | (c12-GAT) | | gatggc |
| | 6 | (c12-GCT) | | gctggc |
| | 7 | (c12-GTT) | | gttggc |
| | 8 | (c13-TGC) | | ggttgc |
| | 9 | (c13-GAC) | | ggtgac |
| | 10 | (c12-AAT) | | aatggc |
| | 11 | (c12-TTT) | | tttggc |
| | 12 | (c12-CTT) | | cttggc |
| | 13 | (c12-AGT, | c13-GAC) | agtgac |

The nucleotide sequence of the K-ras gene is registered as a region from the 5001st to 50675th nucleotides under GenBank Accession No. NG_007524, for example. The nucleotide sequence of SEQ ID NO: 1 is a partial sequence of the K-ras gene and corresponds to a region from the 10351st to 10850th nucleotides in the nucleotide sequence of Accession No. NG_007524. A sequence of codons 12 to 13 corresponds to a region from the 10570th to 10575th nucleotides in the nucleotide sequence of Accession No. NG_007524.

In the present invention, hereinafter, the K-ras gene in which any of nucleotides of codons 12 to 13 is of the mutant-type is referred to as the "mutant-type K-ras gene", and the K-ras gene in which nucleotides of codons 12 to 13 are of the wild-type is referred to as the "wild-type K-ras gene or normal K-ras gene".

In the present invention, a site at which the above-described polymorphism occurs, i.e., a sequence of the 220th to 225th nucleotides in the nucleotide sequence of SEQ ID NO: 1 (sense strand) or a sequence of nucleotides corresponding to the 220th to 225th nucleotides of the sense strand in the complementary strand thereto (antisense strand), is referred to as a "detection target site". In the sequence of SEQ ID NO: 1 (sense strand) or the complementary sequence thereto (antisense strand), a region including the detection target site and to which the probe can hybridize is referred to as a "hybridization region or detection target sequence". Regarding the detection target sequence, the one showing a perfect match with the probe is referred to as a "perfect-match sequence", and the one showing a mismatch with the probe is referred to as a "mismatch sequence". In the present invention, a perfect match means that nucleotides at the detection target site are complementary to nucleotides to be paired therewith in the probe, and preferably means that the detection target sequence is perfectly complementary to the probe. In the present invention, a mismatch means that the nucleotides at the detection target site are not complementary to nucleotides to be paired therewith in the probe, and preferably means that the detection target sequence is perfectly complementary to the probe except for the detection target site.

In the present invention, in the case where the K-ras gene is amplified and further, the probe of the present invention is caused to hybridize with the resultant amplification product, a region to be amplified in the K-ras gene hereinafter is referred to as an "amplification target region". The amplification target region may be, for example, a region in the sense strand of the K-ras gene, a region corresponding thereto in the antisense strand, or both of them. In the present invention, the terms "sense strand" and "antisense strand" encompass, for example, amplification products of the sense strand and amplification products of the antisense strand, respectively.

In the present invention, the ends of a nucleotide sequence mean the endmost nucleotides on the 5' side and the 3' side in the nucleotide sequence. Furthermore, a 5' end region is a region including several nucleotides from the 5' end in a nucleotide sequence, and a 3' end region is a region including several nucleotides from the 3' end in a nucleotide sequence. The several nucleotides mean, for example, 1 to 10, 1 to 4, 1 to 3, or 1 to 2 nucleotides from the end. In the present invention, the Zth nucleotide (Z is a positive integer) from an end of a nucleotide sequence is a numerical order counted with a nucleotide at the end as the first nucleotide. For example, the first nucleotide from the end means the nucleotide at the end, and the second nucleotide from the end means a nucleotide next to the nucleotide at the end.

<Probe for Detecting Polymorphism>

The probe of the present is, as mentioned above, a probe for detecting a polymorphism in a K-ras gene that is a disease-related gene, including at least one of oligonucleotides (P1), (P2), (P3), (P1'), (P2'), and (P3'):

(P1) a 11- to 50-mer oligonucleotide that is composed of a nucleotide sequence complementary to a nucleotide sequence including 220th to 230th nucleotides in SEQ ID NO: 1 and has a nucleotide complementary to the 230th nucleotide in its 5' end region;

(P1') an oligonucleotide composed of a nucleotide sequence complementary to the oligonucleotide (P1);

(P2) a 15- to 50-mer oligonucleotide that is composed of a nucleotide sequence complementary to a nucleotide sequence including 220th to 234th nucleotides in SEQ ID NO: 1 and has a nucleotide complementary to the 234th nucleotide in its 5' end region;

(P2') an oligonucleotide composed of a nucleotide sequence complementary to the oligonucleotide (P2);

(P3) 17- to 50-mer oligonucleotide that is composed of a nucleotide sequence complementary to a nucleotide sequence including 220th to 236th nucleotides in SEQ ID NO: 1 and has a nucleotide complementary to the 236th nucleotide in its 5' end region; and (P3') an oligonucleotide composed of a nucleotide sequence complementary to the oligonucleotide (P3).

Hereinafter, the probe of the present invention is also referred to as a probe for K-ras. The nucleotide length of each of the oligonucleotides (P1) and (P1') is 11- to 50-mer, preferably 13- to 30-mer, and more preferably 15- to 20-mer. The nucleotide length of each of the oligonucleotides (P2) and (P2') is 15- to 50-mer, preferably 15- to 30-mer, and more preferably 15- to 20-mer. The nucleotide length of each of the oligonucleotides (P3) and (P3') is 17- to 50-mer, preferably 17- to 30-mer, and more preferably 17- to 20-mer.

The probe of the present invention is a probe for detecting, a polymorphism in codon 12 of the 220th to 222nd nucleotides (nnt) and a polymorphism in codon 13 of the 223rd to 225th nucleotides (krc) in the partial sequence of SEQ ID NO: 1 in the K-ras gene. Specifically, the probe of the present invention is, for example, a probe for detecting, in the nucleotide sequence of SEQ ID NO: 1, a polymorphism (g/a, g/c, or g/t) of the 220th nucleotide (n), a polymorphism (g/a, g/c, or g/t) of the 221st nucleotide (n), a polymorphism (g/t) of the 223rd nucleotide (k), or a polymorphism (g/a) of the 224th nucleotide (r). In the sequence "nntkrc" of the 220th to 225th nucleotides in the nucleotide sequence of SEQ ID NO: 1, n is guanine (g), adenine (a), cytosine (c), or thymine (t), k is guanine (g) or thymine (t), and r is guanine (g) or adenine (a). The sequence "nntkrc" can be, for example, any of the above-mentioned sequences each having a polymorphism (a wild-type 1 and mutant-types 2-13).

Each of the oligonucleotides (P1), (P2), and (P3) is complementary to the sense strand of the K-ras gene, and the polymorphism can be checked through hybridization of the oligonucleotide with the sense strand, for example. Each of the oligonucleotides (P1), (P2), and (P3) preferably includes a nucleotide sequence (5'-gymann-3') complementary to a nucleotide sequence (5'-nntkrc-3') including 220th to 225th nucleotides in SEQ ID NO: 1. Examples of the sequence "nntkrc" includes the sequences of the above-mentioned wild-type 1 and mutant types 2-13. In the sequence "gymann" that is complementary to the sequence "nntkrc", y is cytosine (c) or thymine (t), m is cytosine (c) or adenine (a), n is guanine (g), adenine (a), cytosine (c), or thymine (t) (the same applies hereinafter).

Each of the oligonucleotides (P1), (P2), and (P3) preferably has a sequence "gccacc" as the sequence "gymann", for example. When the oligonucleotide has this sequence, this sequence shows a perfect match with a wild-type sequence of codons 12 to 13 of the K-ras gene. Therefore, for example, the polymorphism in the K-ras gene can be detected based on whether or not this sequence shows a perfect match with the sequence of codons 12 to 13 in the K-ras gene. Specifically, for example, whether the polymorphism in the K-ras gene is of a wild-type or a mutant-type can be detected, and whether or not the mutant-type K-ras gene has a single-nucleotide mutation or a double-nucleotide mutation can be detected. Hereinafter, the probe including the oligonucleotide having this sequence is referred to as a wild-type probe.

Each of the oligonucleotides (P1), (P2), and (P3) may include a sequence of "gtcact", "gccacg", "gccaca", "gccatc", "gccagc", "gccaac", "gcaacc", "gtcacc", "gccatt", "gccaaa", "gccaag", or "gtcact" as the sequence "gymann", for example. When the oligonucleotide has any of these sequences, the sequence shows a perfect match with any of the sequences of the mutant-types 2-13 of codons 12 to 13. Therefore, the polymorphism in the K-ras gene may be detected through determination of whether or not the sequence shows a perfect match with any of the sequences of the mutant-types 2-13 of codons 12 to 13 of the K-ras gene. Hereinafter, a probe including an oligonucleotide having any of these sequences is referred to as a mutant-type probe.

The oligonucleotide (P1) has a nucleotide complementary to the 230th nucleotide in its 5' end region, preferably at a position of the 1st to 4th nucleotides from the 5' end, more preferably at a position of the 1st to 3rd nucleotides from the same, and particularly preferably at a position of the 2nd nucleotide from the same or the nucleotide at the 5' end. The oligonucleotide (P2) has a nucleotide complementary to the 234th nucleotide in its 5' end region, preferably at a position of the 1st to 4th nucleotides from the 5' end, at a position of the 1st to 3rd nucleotides from the same, and particularly preferably at a position of the 2nd nucleotide from the same or the nucleotide at the 5' end. The oligonucleotide (P3) has a nucleotide complementary to the 236th nucleotide in its 5' end region, preferably at a position of the 1st to 4th nucleotides from the 5' end, more preferably at a position of the 1st to 3rd nucleotides from the same, and particularly preferably at a position of the 2nd nucleotide from the same or the nucleotide at the 5' end.

The oligonucleotide (P1) may be, for example, an oligonucleotide of SEQ ID NO: 3. Examples of the oligonucleotide (P2) includes oligonucleotides of SEQ ID NOs: 4, 5, and 29. The oligonucleotide (P3) may be, for example, an oligonucleotide of SEQ ID NO: 6. In each of the nucleotide sequences of SEQ ID NOs: 3, 4, 5, 6, and 29, the underlined part "gymann"

is a sequence complementary to "nntkrc" that is a detection target site in SEQ ID NO: 1 of the K-ras gene. Among them, a probe including the oligonucleotide of SEQ ID NO: 6 is preferred.

```
                                              (SEQ ID NO: 3)
5'-cctacgymannagctccaactac-3'

(SEQ ID NO: 4)
5'-cttgcctacgymannagctccaactac-3'

(SEQ ID NO: 5)
5'-cttgcctacgymannagctccaactacca-3'

(SEQ ID NO: 29)
5'-cttgcctacgymann-3'

(SEQ ID NO: 6)
5'-ctcttgcctacgymannagctccaact-3'
```

In each of the oligonucleotides (P1), (P2), and (P3), the sequence "gymann" is, as mentioned above, for example, at least one of "gccacc", "gccact", "gccacg", "gccaca", "gccatc", "gccagc", "gccaac", "gcaacc", "gtcacc", "gccatt", "gccaaa", "gccaag", and "gtcact".

The oligonucleotide of SEQ ID NO: 3 may be, for example, an oligonucleotide of SEQ ID NO: 7. The oligonucleotide of SEQ ID NO: 4 may be, for example, an oligonucleotide of SEQ ID NO: 8. The oligonucleotide of SEQ ID NO: 5 may be, for example, an oligonucleotide of SEQ ID NO: 9. The oligonucleotide of SEQ ID NO: 6 may be, for example, an oligonucleotide of SEQ ID NO: 10. In each of the nucleotide sequences, the underlined part "gccacc" is complementary to a detection target site in the sense strand of the wild-type K-ras gene and may be used as a wild-type probe. The oligonucleotide of SEQ ID NO: 29 may be, for example, an oligonucleotide of SEQ ID NO: 30, and the underlined part "gtcacc" is complementary to the sequence of the mutant-type 9 in which codon 13 has a mutation, and may be used as a mutant-type probe. Furthermore, an oligonucleotide of SEQ ID NO: 31 having an additional sequence (a region indicated with capital letters) at the 3' end of SEQ ID NO: 10 may also be used. Among them, a probe including the oligonucleotide of SEQ ID NO: 10 or 31 is preferred.

```
                                              (SEQ ID NO: 7)
5'-cctacgccaccagctccaactac-3'

(SEQ ID NO: 8)
5'-cttgcctacgccaccagctccaactac-3'

(SEQ ID NO: 9)
5'-cttgcctacgccaccagctccaactacca-3'

(SEQ ID NO: 10)
5'-ctcttgcctacgccaccagctccaact-3'

(SEQ ID NO: 31)
5'-ctcttgcctacgccaccagctccaactTGCTGGCTACGC-3'

(SEQ ID NO: 30)
5'-cttgcctacgtcacc-3'
```

The oligonucleotides (P1'), (P2'), and (P3') are, as mentioned above, complementary to the oligoneucleotides (P1), (P2), and (P3), respectively. For example, the oligonucleotides (P1'), (P2'), and (P3') may also be referred to as follows:

(P1') 11- to 50-mer oligonucleotide that is composed of a nucleotide sequence including 220th to 230th nucleotides in SEQ ID NO: 1 and has the 230th nucleotide in its 3' end region;

(P2') 15- to 50-mer oligonucleotide that is composed of a nucleotide sequence including 220th to 234th nucleotides in SEQ ID NO: 1 and has the 234th nucleotide in its 3' end region; and (P3') 17- to 50-mer oligonucleotide that is composed of a nucleotide sequence including 220th to 236th nucleotides in SEQ ID NO: 1 that has the 236th nucleotide in its 3' end region.

Each of the oligonucleotides (P1'), (P2'), and (P3') is homologous to the sense strand of the K-ras gene, and the polymorphism may be checked through hybridization of the oligonucleotide with the antisense strand. In each of the oligonucleotides (P1'), (P2'), and (P3'), the nucleotide sequence complementary to the nucleotide sequence (gymann) of the detection target site in the antisense strand is represented by nntkrc. The sequence "nntkrc" is as mentioned above. When the sequence is of a wild-type, a probe including an oligonucleotide having this sequence is referred to as a wild-type probe. When the sequence is of a mutant-type, a probe including an oligonucleotide having this sequence is referred to as a mutant-type probe.

The oligonucleotide (P1') has the 230th nucleotide in its 3' end region, preferably at a position of the 1st to 4th nucleotides from the 3' end, at a position of the 1st to 3rd nucleotides from the same, particularly preferably at a position of the 2nd nucleotide from the same or the nucleotide at the 3' end. The oligonucleotide (P2') has the 234th nucleotide in its 3' end region, preferably at a position of the 1st to 4th nucleotides from the 3' end, more preferably at a position of the 1st to 3rd nucleotides from the same, particularly preferably at a position of the 2nd nucleotide from the same or the nucleotide at the 3' end. The oligonucleotide (P3') has the 236th nucleotide in its 3' end region, preferably at a position of the 1st to 4th nucleotides from the 3' end, more preferably at a position of the 1st to 3rd nucleotides from the same, particularly preferably at a position of the 2nd nucleotide from the same or the nucleotide at the 3' end.

The probe of the present invention may be, for example, a probe including any of the above-described oligonucleotides or a probe composed of any of the same. In the former case, the probe may further have an additional sequence, for example. It is preferred that each of the oligonucleotides (P1) to (P3) has the additional sequence at its 3' end, for example. The oligonucleotide having the additional sequence may be, for example, the above-mentioned oligonucleotide of SEQ ID NO: 31. It is preferred that each of the oligonucleotides (P1') to (P3') has the additional sequence at its 5' end, for example. The additional sequence of each of the oligonucleotides (P1) to (P3) is, for example, preferably a sequence that is not complementary to the sense strand. The additional sequence of each of the oligonucleotides (P1') to (P3') is, for example, preferably a sequence that is not complementary to the sense strand. The nucleotide length of the additional sequence is, for example, preferably from 1- to 30-mer.

In the probe of the present invention, each of the oligonucleotides (P1) to (P3) may be, for example, an oligonucleotide that is composed of a nucleotide sequence in which one or more nucleotides other than a nucleotide site corresponding to the detection target site and nucleotides complementary to the 230th, 234th, and 236th nucleotides have been deleted, substituted, or added and may hybridize to the detection target sequence. Moreover, in the probe of the present invention, each of the oligonucleotides (P1') to (P3') may be, for example, an oligonucleotide that is composed of a nucleotide sequence in which one or more nucleotides other than a nucleotide site corresponding to the detection target site and the 230th, 234th, and 236th nucleotides have been deleted, substituted, or added and may hybridize to the detection target sequence.

These probes may be used alone or in a combination of two or more of them, for example. When two or more probes are used, it is preferred that the wild-type probe and the mutant-type probe are used in combination, for example. By the combined use, not only detecting a wild-type polymorphism and a mutant-type polymorphism but also identifying the mutant-type polymorphism becomes possible.

The probe of the present invention preferably is a labeled probe having a labeling substance. For example, it is preferable that the oligonucleotide is labeled (modified) with the labeling substance. In the oligonucleotide, a site to be labeled with the labeling substance is not particularly limited, and it preferably is a 5' end region or a 3' end region, more preferably the 5' end or the 3' end, for example. As described below, in the oligonucleotide, a nucleotide to be labeled with the labeling substance preferably is cytosine (c) or guanine (g), for example. The nucleotide may be labeled directly with the labeling substance, or alternatively, it may be labeled indirectly with the labeling substance, for example. In the latter case, for example, by labeling any site in a nucleotide residue containing the nucleotide, the nucleotide may be labeled indirectly with the labeling substance. In each of the above-mentioned oligonucleotides (P1) to (P3), it is preferred that cytosine (c) at its 5' end may have been labeled with the labeling substance, for example. In each of the above-described oligonucleotides (P1') to (P3'), it is preferred that guanine (g) at its 3' end has been labeled with the labeling substance, for example.

Each of the oligonucleotides (P1), (P2), and (P3) preferably has the labeling substance in its 5' end region. Specifically, for example, the labeling substance is located preferably at a position of the 1st the 4th nucleotides from the 5' end, more preferably at a position of the 1st to 3rd nucleotides from the same, and particularly preferably at a position of the 2nd nucleotide from the same or the nucleotide at the 5' end. In the oligonucleotide (P1), for example, it is preferred that the nucleotide complementary to any of the 227th to 233rd nucleotides has the labeling substance, and it is more preferred that the nucleotide complementary to the 230th nucleotide has the labeling substance. In the oligonucleotide (P2), for example, it is preferred that the nucleotide complementary to any of the 231st to 237th nucleotides has the labeling substance, and it is more preferred that the nucleotide complementary to the 234th nucleotide has the labeling substance. In the oligonucleotide (P3), for example, it is preferred that the nucleotide complementary to any of the 233rd to 239th nucleotides has the labeling substance, and it is more preferred that the nucleotide complementary to the 236th nucleotide has the labeling substance.

Each of the oligonucleotides (P1'), (P2'), and (P3') preferably has the labeling substance in its 3' end region. Specifically, for example, the labeling substance is located preferably at a position of the 1st the 4th nucleotides from the 3' end, more preferably at a position of the 1st to 3rd nucleotides from the same, and particularly preferably at a position of the 2nd nucleotide from the same or the nucleotide at the 3' end. In the oligonucleotide (P1'), for example, it is preferred that any of the 227th to 233rd nucleotides has the labeling substance, and it is more preferred that the 230th nucleotide has the labeling substance, for example. In the oligonucleotide (P2'), for example, it is preferred that any of the 231st to 237th nucleotides has the labeling substance, and it is more preferred that the 234th nucleotide has the labeling substance. In the oligonucleotide (P3'), for example, it is preferred that any of the 233rd to 239th nucleotides has the labeling substance, and it is more preferred that the 236th nucleotide has the labeling substance.

The labeling substance is not particularly limited, and preferably is the one that gives off signals depending on whether the labeled probe is present independently or it forms a hybrid, for example. The type of the signal is not particularly limited, and examples of the signal include fluorescence and coloring. When the signal is fluorescence, examples of a signal value include fluorescence intensity and the like. When the signal is coloring, examples of a signal value include reflectance, absorbance, and transmittance. The signal may be given off from the labeling substance directly or indirectly, for example.

The labeling substance is not particularly limited, and examples thereof include fluorescent substances such as a fluorophore and the like. Examples of the fluorescent substance include fluorescein, phosphor, rhodamine, and polymethine dye derivatives. Examples of commercially available fluorescent substances include PACIFIC BLUE (registered trademark, produced by Molecular Probes), BODIPY FL (registered trademark, produced by Molecular Probes), FluorePrime (trade name, produced by Amersham Pharmacia), Fluoredite (trade name, produced by Millipore Corporation), FAM (registered trademark, produced by ABI), Cy3 and Cy5 (trade names, produced by Amersham Pharmacia), and TAMRA (registered trademark, produced by Molecular Probes). The detection condition for the fluorescent substance is not particularly limited, and may be determined as appropriate depending on the type of the fluorescent substance to be used, for example. For example, PACIFIC BLUE may be detected at a detection wavelength from 450 to 480 nm, TAMRA may be detected at a detection wavelength from 585 to 700 nm, and BODIPY FL may be detected at a detection wavelength from 515 to 555 nm. When such a labeled probe is used, for example, by detecting fluorescence as a signal and measuring a fluorescence intensity as a signal value, hybridization and dissociation may be checked easily based on the change in fluorescence intensity.

Preferably, the labeled probe is, for example, a labeled probe that shows signals independently and shows no signals when it forms a hybrid, or a labeled probe that shows no signals independently and shows signals when it forms a hybrid. In the case where the labeling substance is a fluorescent substance, the labeled probe preferably is a probe that is labeled with the fluorescent substance and shows fluorescence independently, and shows reduced (e.g., quenched) fluorescence when it forms a hybrid, for example. Such a phenomenon generally is called a fluorescence quenching phenomenon. Probes utilizing this phenomenon generally are called fluorescence quenching probes. Among these fluorescence quenching probes, preferred is, for example, the one in which the 3' end or the 5' end of the oligonucleotide is labeled with the fluorescent substance, and the nucleotide at the end to be labeled preferably is cytosine (c) or guanine (g). In the case where the nucleotide at the end is cytosine (c), the nucleotide sequence of the fluorescence quenching probe preferably is designed so that, for example, when the fluorescence quenching probe forms a hybrid with a test nucleic acid, a nucleotide to be paired with the labeled cytosine (c) at the end or a nucleotide apart therefrom by one to three nucleotides in the test nucleic acid is guanine (g). A nucleotide away from the nucleotide to be paired with cytosine (c) by one nucleotide is a nucleotide located next to the nucleotide to be paired with cytosine (c). Such a probe generally is called a guanine quenching probe, and is known as a so-called QPROBE (registered trademark). When such a guanine quenching probe hybridizes to the test nucleic acid, there occurs a phenomenon that, for example, as the fluorescent substance-labeled cytosine (c) at the end approaches guanine (g) in the test nucleic acid, fluorescence of the fluorescent substance becomes weak, in other words, the fluorescence intensity is reduced. By using such a probe, hybridization and dissociation may be checked easily based on the change in fluorescence intensity. Similarly, in the case where the above-described nucleotide at the end is guanine (g), the nucleotide sequence of the fluorescence quenching probe may be designed so that, for example, when the fluorescence quenching probe forms a hybrid with a test nucleic acid, a nucleotide to be paired with the labeled guanine (g) at the end or a nucleotide apart therefrom by one to three nucleotides in the test nucleic acid is cytosine (c).

In the probe of the present invention, for example, a phosphate group may be added to the 3' end. As described below, a test nucleic acid may be prepared by a nucleic acid amplification method such as PCR, for example. At this time, the probe of the present invention may be caused to be present in a reaction system of the nucleic acid amplification reaction. In such a case, when the 3' end of the probe has a phosphate group added thereto, it is possible to sufficiently prevent the probe itself from being elongated by the nucleic acid amplification reaction. A similar effect is obtained also by adding a labeling substance such as described above to the 3' end.

In the detection of the polymorphism using the probe of the present invention, the detection method is by no means limited as long as it is a method utilizing the hybridization of the detection target sequence and the probe. As the method for detecting the polymorphism, the polymorphism detection method according to the present invention is described below.

<Method for Detecting Polymorphism>

The method for detecting a polymorphism according to the present invention is, as mentioned above, a method for detecting a polymorphism in a disease-related gene, including the step of: detecting a polymorphism in a K-ras gene using the probe of the present invention.

For example, the method of the present invention preferably includes the steps of:
  (A) while changing a temperature of a reaction system containing a test nucleic acid for detecting the polymorphism and the probe of the present invention, measuring a signal value indicating a melting state of a hybrid between the test nucleic acid and the probe; and
  (B) detecting the polymorphism in the test nucleic acid based on change in the signal value accompanying the temperature change.

The method of the present invention is characterized in that it uses the probe of the present invention, and other configurations, conditions, and the like are not limited to those described below. As described above, the probe of the present invention preferably is a labeled probe. In the present invention, the reaction system is a reaction solution, for example.

In the present invention, the test nucleic acid may be a single-stranded nucleic acid or a double-stranded nucleic acid. When the test nucleic acid is a double-stranded nucleic acid, the step (A) preferably includes the step of dissociating the double-strand test nucleic acid by heating the reaction system, for example, as described below. By dissociating the double-stranded nucleic acid into single-stranded nucleic acids, the probe of the present invention can hybridize with the single-stranded nucleic acid.

In the present invention, the test nucleic acid may be a nucleic acid contained inherently in a sample or an amplification product of the nucleic acid, for example. The latter is preferable because, for example, it allows the detection accuracy to be improved. The amplification product may be prepared by amplifying the nucleic acid in the sample as a template nucleic acid according to a nucleic acid amplification method, for example. The amplification product may be an amplification product obtained by using DNA in the sample as a template or an amplification product obtained by using cDNA synthesized from RNA in the sample as a template, for example. Examples of the RNA in the sample include RNAs such as total RNA and mRNA, and the cDNA may be synthesized from, for example, the RNA such as described above by, for example, RT-PCR (Reverse Transcription PCR).

For example, in the case where the test nucleic acid is the amplification product, the method of the present invention may further include, for example, the following step (X):
  (X) producing the amplification product from a template nucleic acid.

The step (X) preferably is performed prior to the step (A), for example. The step (X) may be the step of producing the amplification product from the template nucleic acid in the reaction system in the presence of the probe, for example.

In the step (A), it is only necessary that the probe is contained in the reaction system, and the timing of adding the probe is not particularly limited, for example. In the case where the test nucleic acid is the amplification product, the reaction system in the step (A) may be prepared newly using the amplification product obtained in the step (X) and the probe, or may be the reaction system of the amplification reaction in the step (X), for example. In the latter case, the probe may be added to the reaction system of the amplification reaction before or during the step (X), for example. Alternatively, the probe may be added to the reaction system after the step (X).

The method for amplifying the nucleic acid is not particularly limited, and examples thereof include a PCR (Polymerase Chain Reaction) method, a NASBA (Nucleic Acid Sequence Based Amplification) method, a TMA (Transcription-Mediated Amplification) method, and a SDA (Strand Displacement Amplification) method. Among them, the PCR method is preferable. The conditions of the method for amplifying the nucleic acid are not particularly limited, and the method can be carried out using conventionally known techniques.

In the production of the amplification product from the template nucleic acid, it is preferable to use a primer for amplifying a region including a detection target polymorphism (hereinafter also referred to as a "primer for K-ras") in the K-ras gene. The sequence of the primer is not particularly limited as long as a detection target sequence including the detection target site may be amplified, for example, and the sequence of the primer may be set as appropriate by a conventionally known method, depending on the detection target sequence, sequences in the vicinity thereof, and the like. The length of the primer is not particularly limited, and may be set to a general length. For example, the length of the primer may be 10- to 40-mer.

As the primer for K-ras, for example, either one of a forward primer (hereinafter also referred to as an "F primer") for amplifying the sense strand of the gene and a reverse primer (hereinafter also referred to as an "R primer") for amplifying the antisense strand of the gene may be used. It is preferable to use a primer set including a pair composed of these primers. Examples of the F primer and the R primer are shown below. It is to be noted that they are merely illustrative and by no means limit the present invention.

(F primer)
F1
(SEQ ID NO: 11)
5'-accttatgtgtgacatgttctaatatagtcacattttc-3'

F2
(SEQ ID NO: 12)
5'-aaggcctgctgaaaatgactg-3'

F1-LP
(SEQ ID NO: 32)
5'-ggtactggtggagtatttgatagtgt-3'

(R primer)
R2
(SEQ ID NO: 18)
5'-ggtcctgcaccagtaatatgca-3'

R1-LP
(SEQ ID NO: 33)
5'-gaattagctgtatcgtmaaggcactc-3'
m = c or a

R3-LP
(SEQ ID NO: 34)
5'-cacaaaatgattctgaattagctgtatcg-3'

The F primer and the R primer may be, for example, primers designed so that they may anneal to a region including a whole sequence or a partial sequence of codons 12 to 13, for example. In this case, the sequence of codons 12 to 13 may be set to a wild-type sequence, for example. It is, however, preferred that the sequence is set to a mutant-type sequence. By setting the sequence to be of a mutant-type, the mutant-type detection target sequence may be amplified efficiently even when the amount of the mutant-type K-ras gene is small, for example. Examples of the R primer are shown below. It is to be noted that they are merely illustrative and by no means limit the present invention. In each of the following sequences, the underlined part is a sequence complementary to the whole sequence (nntkrc) or the partial sequence of codons 12 to 13, and the nucleotide indicated with a capital letter is a nucleotide complementary to the mutant-type polymorphism. The R-WT primer is a primer that has a sequence complementary to a sequence "ggtggc" that is the whole sequence (nntkrc) and amplifies a wild-type target site. Each of the R-c12-XGT, R-c12-GXT, and R-c13-TGC is a primer that amplifies a mutant-type target site. The R-c12-XGT has a sequence complementary to a sequence "ngtggc" that is the whole sequence (nntkrc). The R-c12-GXT has a sequence complementary to a sequence "ntggc" that is the partial sequence (ntkrc). The R-c13-TGC has a sequence complementary to a sequence "tgc" that is a whole sequence (lac) of codon 13. The R-c13-GAC has a sequence complementary to a sequence "ac" that is a partial sequence (rc) of codon 13.

```
(R primer)
R-WT
                                       (SEQ ID NO: 13)
5'-ctcttgcctacgccacc-3'

R-c12-XGT
                                       (SEQ ID NO: 14)
5'-cactcttgcctacgccacD-3'
D = t, g, or a R-c12-GXT
                                       (SEQ ID NO: 15)
5'-gcactcttgcctacgccaD-3'
D = t, g, or a R-c13-TGC
                                       (SEQ ID NO: 16)
5'-caaggcactcttgcctacgcA-3'

R-c13-GAC
                                       (SEQ ID NO: 17)
5'-tcaaggcactcttgcctacgT-3'
```

In the present invention, the combination of the primers is not particularly limited, and for example, it is preferable to use an F primer and an R primer as a primer set composed of them. Further, with respect to at least one of the F primer and the R primer, it is preferred that a primer for amplifying a wild-type detection target region and a primer for amplifying a mutant-type detection target region are used in combination. Specifically, an F primer, an R primer for amplifying a wild-type detection target region, and an R primer for amplifying a mutant-type detection target region are used in combination. The primer for amplifying a wild-type detection target region is also referred to as a wild-type primer, and the primer for amplifying a mutant-type detection target region is also referred to as a mutant-type primer. By using the wild-type primer and the mutant-type primer in combination as mentioned above, a mutant-type detection target region may be detected with high accuracy even when the amount of the mutant-type K-ras gene is small, for example. Examples of the combination of the F primer and the R primers include a combination of at least one of an F1 primer and an F2 primer, an R-WT primer, an R-c12-XGT primer, and an R-c12-GXT primer and a combination of at least one of an F1 primer and an F2 primer, and an R-WT primer, an R-c13-TGC primer, and an R-c13-GAC primer. Moreover, for example, a combination of an F1-LP primer (SEQ ID NO: 32) and an R1-LP primer (SEQ ID NO: 33) or an R3-LP (SEQ ID NO: 34) also is preferable.

In the reaction system, the proportion of the primer to be added is not particularly limited. For example, the proportion of one type of primer to be added in the reaction system is, for example, 0.1 to 2 μmol/l, preferably 0.25 to 1.5 μmol/l, and particularly preferably 0.5 to 1 μmol/l. When an F primer and an R primer are used, the ratio (the molar ratio F:R) between the F primer (F) and R primer (R) to be added is not particularly limited, and is, for example, preferably from 1:0.25 to 1:4, more preferably from 1:0.5 to 1:2.

In the step (A), the ratio (molar ratio) of the probe according to the present invention to be added relative to the test nucleic acid is not particularly limited. It preferably is 1 or less because this allows detection signals to be secured sufficiently. At this time, the amount of the test nucleic acid may be, for example, the total amount of a perfect match nucleic acid having a perfect match sequence and a mismatch nucleic acid having a mismatch sequence, or may be the total amount of an amplification product containing a perfect match sequence and an amplification product containing a mismatch sequence. Although the proportion of the perfect match nucleic acid in the test nucleic acid generally is unknown, it is preferable that the ratio (molar ratio) of the probe to be added relative to the perfect match nucleic acid (the amplification product containing the perfect match sequence) eventually becomes 10 or less, more preferably 5 or less, and still more preferably 3 or less. The lower limit of the ratio is not particularly limited, and is, for example, 0.001 or more, preferably 0.01 or more, and more preferably 0.1 or more. The ratio of the probe of the present invention to be added relative to the test nucleic acid may be the molar ratio thereof relative to a double-stranded nucleic acid or relative to a single-stranded nucleic acid, for example.

The proportion of the probe of the present invention to be added in the reaction system is not particularly limited. For example, it is preferable to add one type of the probe so that its concentration is in the range from 10 to 1000 nmol/l, more preferably from 20 to 500 nmol/l. In the reaction solution, the molar ratio of the probe relative to the test nucleic acid preferably is, for example, 1 or less, because this allows sufficient signal values to be secured, for example. The ratio of the probe to be added relative to the test nucleic acid may be the molar ratio thereof relative to a double-stranded nucleic acid or relative to a single-stranded nucleic acid, for example.

A sample to which the polymorphism detection method of the present invention is applied is not particularly limited, and examples thereof include biological samples. Specific examples of the biological samples include: tissues such as a large intestine, rectum, and pancreas; whole blood; blood cells such as leukocyte cells; oral cells such as oral mucosa; somatic cells such as nails and hairs; germ cells; sputum; amniotic fluid; paraffin-embedded tissues; urine; gastric juice; and liquid obtained by gastrolavage. In the present invention, a method for collecting the sample, a method for preparing a test nucleic acid from the sample, and the like are not particularly limited, and any conventionally known methods can be employed.

The polymorphism detection method of the present invention may be utilized in so-called Tm analysis (also called melting curve analysis) such as mentioned above. The following is an explanation of a Tm value in the Tm analysis. For example, when a solution containing a double-stranded DNA is heated, an absorbance at 260 nm increases. This is caused by the fact that the hydrogen bond between the strands composing the double-stranded DNA is unbound by the heating, whereby the double-stranded DNA is dissociated into single-stranded DNAs (melting of DNA). Then, when every double-stranded DNA is dissociated into single-stranded DNAs, the absorbance of the solution becomes about 1.5 times as large as the absorbance at the time when the heating was initiated (i.e., the absorbance of the solution containing only the double-stranded nucleic acid), whereby it may be determined that the melting is completed. Based on this phenomenon, a melting temperature Tm generally is defined as a temperature at the time when the amount of increase in absorbance reaches 50% of the total amount of increase in absorbance.

In the step (A), the measurement of a signal indicating the melting state of a hybrid between the test nucleic acid and the probe may be, for example, the measurement of an absorbance at 260 nm as mentioned above or the measurement of a signal of the labeling substance. Specifically, it is preferable that a labeled probe labeled with the labeling substance may be used as the probe as mentioned above and that a signal of the labeling substance is measured. The labeled probe may be, for example, a labeled probe that shows signals independently and shows no signals when it forms a hybrid, or a labeled probe that shows no signals independently and shows signals when it forms a hybrid. The former probe does not show signals when it forms a hybrid (double-stranded DNA) with the amplification product and shows signals when the probe is dissociated from the amplification product by heating. On the other hand, the latter probe shows signals when it forms a hybrid (double-stranded DNA) with the amplification product, and the signals are reduced (quenched) when the probe is dissociated from the amplification product by heating. Therefore, by detecting signals of the labeling substance, the detection of the progress of the melting of the hybrid, the determination of the Tm value, and the like may be achieved, as in the case where the absorbance at 260 nm is measured. The signal of the labeling substance may be detected under the condition specific to the signal of the labeling substance, for example. Examples of the condition include an excitation wavelength and a detection wavelength. The labeled probe and the labeling substance are as mentioned above.

In the step (B), the detection of the polymorphism based on change in the signal value may be performed by a conventional method. As a specific example, for example, the change in signal value is compared with the change in hybrid between the probe and a mutant-type detection target sequence and/or the change in hybrid between the probe and a wild-type detection target sequence, and whether the polymorphism is of a mutant-type or a wild-type may be determined. That is, when the polymorphism is the same as the mutant-type detection target sequence, it is determined as a mutant-type polymorphism, and when it is the same as the wild-type detection target sequence, it is determined as a wild-type polymorphism. On the other hand, for example, the polymorphism may be determined through determination of the Tm value based on the change in signal and comparison of Tm values. First, a Tm value is determined based on the change in signal value. Then, the measured Tm value is compared with a $Tm_{wt}$ value with respect to the wild-type detection target sequence and/or a $Tm_{mt}$ value with respect to the mutant-type detection target sequence. When the measured Tm value is the same or about the same as the $Tm_{wt}$ value with respect to the wild-type detection target sequence, it is determined that the polymorphism is of a wild-type. When it is lower that the $Tm_{wt}$ value, it is determined that the polymorphism is of a mutant-type. When it is the same or about the same as the $Tm_{mt}$ value with respect to the mutant-type detection target sequence, it is determined that the polymorphism is of a mutant-type. When it is lower than the $Tm_{mt}$ value, it is determined that the polymorphism is of a wild-type. The temperature about the same as the Tm value means, for example, the temperature in the range of ±3° C. of the Tm value.

Next, the polymorphism detection method of the present invention is described with reference to an illustrative example. The present example is directed to the case where the probe of the present invention is a labeled probe labeled with a fluorescent substance, a template nucleic acid is amplified in the presence of the probe, and the resultant amplification product is used as the test nucleic acid. The method of the present invention is characterized in that the probe of the present invention is used in the method, and the other steps and conditions are by no means limited.

First, genomic DNA is isolated from the biological sample. Isolation of the genomic DNA from the biological sample may be achieved by a conventionally known method. Specifically, the isolation may be achieved using a commercially available genomic DNA isolation kit (trade name "GFX Genomic Blood DNA Purification kit"; GE Healthcare Bio-Sciences) or the like, for example.

Next, a reaction solution is prepared by adding a labeled probe to a sample containing the isolated genomic DNA. As the labeled probe, for example, QPROBE (registered trademark) is preferable, as mentioned above.

The labeled probe may be added to the sample containing the isolated genomic DNA or may be mixed with the genomic DNA in a solvent, for example. The solvent is not particularly limited, and examples thereof include conventionally known solvents including: buffer solutions such as Tris-HCl and the like; solvents respectively containing KCl, $MgCl_2$, $MgSO_4$, glycerol, and the like; and reaction solutions for nucleic acid amplification, such as reaction solutions for PCR.

The timing of adding the labeled probe is not particularly limited. For example, the labeled probe may be added before, during, or after the nucleic acid amplification reaction. In particular, it is preferable to add the labeled probe to the reaction solution before the nucleic acid amplification reaction because, for example, it is not necessary to expose the reaction solution to the external environment in order to add the labeled probe and it is possible to carry out the nucleic acid amplification reaction and the measurement of signal values successively. In this case, it is preferable that the 3' end of the labeled probe is modified with the labeling substance or a phosphate group, as mentioned above.

Subsequently, using the isolated genomic DNA as a template, a sequence including a detection target site in which a detection target polymorphism occurs is amplified in the presence of the labeled probe by a nucleic acid amplification method such as PCR. Although the present invention is described using the case where PCR is used as the nucleic acid amplification method as an example, the present invention is not limited thereto. Also, conditions for the PCR are not particularly limited, and the PCR may be carried out according to a conventionally known method.

Specifically, the reaction solution containing the genomic DNA, the labeled probe, and the primer is subjected to PCR. The composition of the reaction solution is not particularly limited, and those skilled in the art may set the composition as appropriate. In addition to the genomic DNA, the labeled probe, and the primer, the reaction solution further may contain: a polymerase such as DNA polymerase; nucleoside triphosphate; a buffer solution; any of various types of catalysts; and the like, for example. The proportions of the labeled probe and the primer to be added in the reaction solution are not particularly limited, and they may be in the above-mentioned ranges, respectively, for example.

The DNA polymerase is not particularly limited, and conventionally known polymerases derived from heat-resistant bacteria can be used, for example. As specific examples of such polymerases, *Thermus aquaticus*-derived DNA polymerases (U.S. Pat. Nos. 4,889,818 and 5,079,352) (trade name "Taqpolymerase"), *Thermus thermophilus*-derived DNA polymerase (WO 91/09950) (rTth DNA polymerase), *Pyrococcus furiosus*-derived DNA polymerase (WO 92/9689) (Pfu DNA polymerase, produced by Stratagenes), *Thermococcus litoralis*-derived polymerase (EP-A 455 430 (trademark "Vent"), produced by New England Biolabs), and the like, for example, are commercially available. Among them, *Thermus aquaticus*-derived heat-resistant DNA polymerases are preferable.

The proportion of the DNA polymerase to be added in the reaction solution is not particularly limited, and is, for example, 1 to 100 U/ml, preferably 5 to 50 U/ml, and more preferably 20 to 40 U/ml. With regard to the unit of activity (U) of DNA polymerases, 1 U generally is defined as an activity for incorporating 10 nmol of entire nucleotide into acid-insoluble precipitate at 74° C. in 30 minutes in a reaction solution for activity measurement using activated salmon sperm DNA as a template primer. The composition of the reaction solution for activity measurement is as follows, for example: 25 mmol/l TAPS buffer (pH 9.3, 25° C.), 50 mmol/l KCl, 2 mmol/l MgCl$_2$, 1 mmol/l mercaptoethanol, 200 μmol/l dATP, 200 μmol/l dGTP, 200 μmol/l dTTP, 100 μmol/l [α-$^{32}$P] dCTP, and 0.25 mg/mL activated salmon sperm DNA.

The nucleoside triphosphate generally is dNTP (dATP, dCTP, dGTP, and dTTP or dUTP). The proportion of dNTP to be added in the reaction solution is not particularly limited, and is, for example, 0.01 to 1 mmol/l, preferably 0.05 to 0.5 mmol/l, and more preferably 0.1 to 0.3 mmol/l.

Examples of the buffer solution include Tris-HCl, Tricine, MES, MOPS, HEPES, and CAPS, and it is possible to use commercially available buffer solutions for PCR and buffer solutions included in commercially available PCR kits.

The reaction solution further may contain heparin, betaine, KCl, MgCl$_2$, MgSO$_4$, glycerol, or the like, and the proportions of these components to be added may be set within ranges where they do not interfere with the PCR reaction, for example.

The total volume of the reaction solution is not particularly limited, and can be determined as appropriate depending on a device to be used, such as a thermal cycler, and the like, for example. The total volume generally is 1 to 500 preferably 10 to 100 μl.

Next, PCR is conducted. The cycle conditions of the PCR are not particularly limited. For example, for (1) dissociation of a double-strand DNA as a test nucleic acid into single-stranded DNAs; (2) annealing of the primer to the single-stranded DNA; and (3) elongation of the primer through a polymerase reaction, conditions shown in Table 1 below may be employed. The number of cycles in the PCR is not particularly limited. It is preferably 30 cycles or more with the three steps described in the following items (1) to (3) as one cycle, for example. The upper limit of the total number of cycles is not particularly limited and is, for example, 100 cycles or less, preferably 70 cycles or less, and more preferably 50 cycles or less. The temperature change in each of the steps may be controlled automatically using a thermal cycler or the like, for example.

TABLE 1

| | Temperature (° C.) and Time (seconds) |
|---|---|
| (1) Dissociation into single-stranded DNAs | e.g., 90° C. to 99° C., 1 to 120 seconds preferably, 92° C. to 95° C., 1 to 60 seconds |
| (2) Annealing of primer | e.g., 40° C. to 70° C., 1 to 300 seconds preferably, 50° C. to 70° C., 5 to 60 seconds |
| (3) Elongation reaction | e.g., 50° C. to 80° C., 1 to 300 seconds preferably, 50° C. to 75° C., 5 to 60 seconds |

The proportion of the labeled probe to be added in the reaction solution is not particularly limited. For example, it is preferred that the labeled probe is added so that its concentration is in the range from 10 to 1000 nmol/l, more preferably from 20 to 500 nmol/l. In the reaction solution, the molar ratio of the labeled probe relative to the test nucleic acid is, for example, preferably 1 or less, because this allows sufficient signal value to be secured, for example. The ratio of the labeled probe to be added relative to the test nucleic acid may be, for example, the molar ratio thereof relative to a double-stranded nucleic acid or relative to a single-stranded nucleic acid.

Next, dissociation of the obtained amplification product (double-stranded DNA) and hybridization of a single-stranded DNA obtained through the dissociation and the labeled probe are caused. This can be achieved by, for example, changing the temperature of the reaction solution in the presence of the labeled probe. In this case, it is preferred that the reaction solution to which the labeled probe has been already added is subjected to an amplification reaction, after which the temperature of the reaction solution is changed, as mentioned above.

The heating temperature in the disassociation step is not particularly limited as long as it is a temperature at which the double-stranded amplification product may be disassociated into single strands. The heating temperature is, for example, from 85° C. to 95° C. The heating time is not particularly limited, and generally is from 1 second to 10 minutes, preferably from 1 second to 5 minutes.

The hybridization of the labeled probe with the disassociated single-stranded DNA may be achieved by, for example, lowering the heating temperature in the disassociation step after the completion of the disassociation step. The temperature condition is, for example, from 40° C. to 50° C. The time period for conducting a treatment at this temperature is not particularly limited, and is, for example, from 1 to 600 seconds.

Then, signal values indicating the melting states of the hybrid between the amplification product and the labeled probe are measured while changing the temperature of the reaction solution. Specifically, for example, the reaction solution (the hybrid between the single-stranded DNA and the labeled probe) is heated, and change in signal value accompanying the temperature rise is measured. As mentioned above, in the case where a guanine quenching probe, i.e., a probe in which cytosine (c) at the end is labeled, is used, fluorescence is reduced (or quenched) in the state where the probe hybridizes with the single-stranded DNA, and fluorescence is emitted in the state where the probe is disassociated. Therefore, in this case, the hybrid with reduced (quenched) fluorescence may be heated gradually, and increase in fluorescence intensity accompanying the temperature rise may be measured, for example.

When measuring the change in fluorescence intensity, the temperature range used in the measurement is not particularly limited. The initiation temperature is, for example, from room temperature to 85° C., preferably from 25° C. to 70° C., and the end temperature is, for example, from 40° C. to 105° C. The temperature rising rate is not particularly limited, and is, for example, from 0.1 to 20° C./sec., preferably from 0.3 to 5° C./sec.

Next, the Tm value is determined by analyzing the change in signal value. Specifically, from the obtained fluorescence intensities, the amount of change in fluorescence intensity per unit time (−d amount of increase in fluorescence intensity/dt) at each temperature is calculated, and a temperature at which the amount of change is smallest may be determined as the Tm value. A temperature at which the amount of increase in fluorescence intensity per unit time (d amount of increase in fluorescence intensity/t) is largest may also be determined as the Tm value. When a probe that shows no signals independently and shows signals when it forms a hybrid is used as the labeled probe instead of the fluorescence quenching probe, the amount of decrease in fluorescence intensity may be measured, contrary to the case stated above. For example, in the case where a plurality of labeled probes respectively labeled with labeling substances that are detected at different detection wavelengths are used in place of the labeled probe, the change in signal value may be analyzed at each detection wavelength.

The Tm value may be calculated using MELTCALC software (meltcalc.com), which is known conventionally, or the like, for example. Also, the Tm value may be determined by a nearest neighbor method.

Then, based on the Tm value, it is determined whether any of the 220th, 221th, 223th or 224th nucleotides in the nucleotide sequence shown in SEQ ID NO: 1 of the K-ras gene is of the wild-type or the mutant type in the detection target sequence. In the Tm analysis, a perfectly complementary hybrid (match) exhibits a higher Tm value, which indicates dissociation, than a hybrid with one or several different nucleotides (mismatch). Therefore, with regard to the labeled probe, by determining the Tm value of a perfectly complementary hybrid and the Tm value of a hybrid with difference in one or several nucleotides beforehand, it is possible to determine whether the nucleotide in the detection target sequence is of the wild type or the mutant type. Furthermore, as mentioned above, by using the wild-type detection probe and the mutant-type detection probes in combination, the type of the polymorphism may be determined based on which of the probes shows the Tm value of the perfectly complementary hybrid.

In the present invention, instead of raising the temperature of the reaction system containing the probe (heating the hybrid), and then measuring the change in signal accompanying the temperature rise as mentioned above, the change in signal at the time of hybrid formation may be measured, for example. That is, when forming a hybrid by lowering the temperature of the reaction system containing the probe, the change in signal accompanying the temperature lowering may be measured.

As a specific example, in the case where a labeled probe that shows signals independently and shows no signals when it forms a hybrid (e.g., a guanine quenching probe) is used, the labeled probe emits fluorescence in the state where a single-stranded DNA and the labeled probe are dissociated, and the fluorescence is reduced (or quenched) when the temperature is lowered to allow the labeled probe to form a hybrid. Therefore, in this case, the temperature of the reaction solution may be lowered gradually, and decrease in fluorescence intensity accompanying the temperature lowering may be measured, for example. On the other hand, when a labeled probe that shows no signals independently and shows signals when it forms a hybrid is used, the labeled probe does not emit fluorescence in the state where the single-stranded DNA and the labeled probe are dissociated, and the labeled probe emits fluorescence when the temperature is lowered to allow the labeled probe to form a hybrid. Therefore, in this case, the temperature of the reaction solution may be lowered gradually, and increase in fluorescence intensity accompanying the temperature lowering may be measured, for example.

In the polymorphism detection method of the present invention, for example, the probe of the present invention and a probe for detecting a polymorphism in a gene other than a K-ras gene may be used in combination. A polymorphism(s) in two or more types of genes including the K-ras gene may be detected in the same reaction system through the combined use of the probe of the present invention and the probe for detecting a gene other than the K-ras gene. The gene other than the K-ras gene may be, for example, a BRAF gene that is a disease-related gene as well as the K-ras gene. Therefore, a polymorphism(s) in the K-ras gene and the BRAF gene that are related to diseases may be detected. Clinical cases of the above-mentioned diseases where a polymorphism in the K-ras gene is of a wild-type and a polymorphism in the BRAF gene is of a mutant type have been reported. Therefore, by detecting the presence or absence of mutation (polymorphism) in the BRAF gene in addition to the K-ras gene, for example, accuracy of diagnoses of the above-mentioned diseases, selections of more effective treatment methods for the diseases, and the like may be further improved.

A detection target polymorphism in the BRAF gene is such that, in a partial sequence of SEQ ID NO: 2 in the BRAF gene, the 229th nucleotide (w) is thymine (t) when the nucleotide is of a wild type and is adenine (a) when the nucleotide is of a mutant type, for example. When the nucleotide is of a wild type (t), the 600th amino acid in the BRAF protein is valine (V), and when the nucleotide is of a mutant type (a), the 600th amino acid in the BRAF protein is glutamic acid (E). When the BRAF gene is of a mutant type as mentioned above, for example, it may be determined that the subject has possibilities of having any of the above-mentioned diseases and having drug resistance.

The nucleotide sequence of the BRAF gene is registered as a region from 5001st to 195753rd nucleotides under GenBank accession No. NG_007873, for example. The nucleotide sequence of SEQ ID NO: 2 is a partial sequence of the BRAF gene and corresponds to a region from 176201st to 176700th nucleotides in the nucleotide sequence of the Accession No. NG_007873. The detection target site corresponds to the 176429th nucleotide in the nucleotide sequence of the Accession No. NG_007873. In the nucleotide sequence of SEQ ID NO: 2, w is adenine or thymine.

Hereinafter, the BARF gene in which the 229th nucleotide (w) in the nucleotide sequence of SEQ ID NO: 2 is of a mutant-type is referred to as the "mutant-type BRAF gene", and the BRAF gene in which the 229th nucleotide (w) is of a wild-type is referred to as the "wild-type BRAF gene or normal BRAF gene".

Hereinafter, the probe for detecting a polymorphism in a BRAF gene is also referred to as a "probe for BRAF". The probe for BRAF is not particularly limited and may be, for example a probe including at least one of oligonucleotides (P4) and (P4'):

(P4) a 9- to 50-mer oligonucleotide that is composed of a nucleotide sequence including 229th to 237th nucleotides in SEQ ID NO: 2 and has the 237th nucleotide in its 3' end region; and (P4') an oligonucleotide composed of a nucleotide sequence complementary to the oligonucleotide (P4).

The nucleotide length of each of the oligonucleotides (P4) and (P4') is 9- to 50-mer, preferably 10- to 50-mer, more preferably 13- to 30-mer, and yet more preferably 15- to 20-mer.

The oligonucleotide (P4) is, for example, homologous to the sense strand of the BRAF gene, and a polymorphism may be checked through hybridization of the oligonucleotide with the antisense strand.

The oligonucleotide (P4) has the 237th nucleotide in its 3' end region, preferably at a position of the 1st to 4th nucleotides from its 3' end, more preferably at a position of the 1st to 3rd nucleotides from the same, and particularly preferably at a position of 2nd nucleotide from the same or the nucleotide at the 3' end.

Examples of the oligonucleotide (P4) include oligonucleotides of SEQ ID NOs: 19 and 35. In each of the nucleotide sequences of SEQ ID NOs: 19 and 35, an underlined part w is a nucleotide homologous to the detection target site w in the BRAF gene of SEQ ID NO: 2. When w is a (SEQ ID NOs: 27 and 36) in SEQ ID NOs: 19 and 35, the probe shows a perfect match with a detection target sequence of the mutant-type BRAF gene. Such a probe is also referred to as a mutant-type probe. In contrast, when w is t (SEQ ID NOs: 28 and 37) in SEQ ID NOs: 19 and 35, the probe shows a perfect match with a detection target sequence of the wild-type BRAF gene. Such a probe is also referred to as a wild-type probe. Therefore, the polymorphism in the BRAF gene may be detected based on whether or not the oligonucleotides show a perfect match with the detection target sequence in the BRAF gene. They are merely illustrative and by no means limit the present invention.

(Probe for BRAF)
(SEQ ID NO: 19)
5'-ctagctacag<u>w</u>gaaatctc-3'

(SEQ ID NO: 27)
5'-ctagctacagagaaatctc-3'

(SEQ ID NO: 28)
5'-ctagctacagtgaaatctc-3'

(SEQ ID NO: 35)
5'-gctacag<u>w</u>gaaatctc-3'

(SEQ ID NO: 36)
5'-gctacagagaaatctc-3'

(SEQ ID NO: 37)
5'-gctacagtgaaatctc-3'

The oligonucleotide (P4') is complementary to the oligonucleotide (P4) as mentioned above. The oligonucleotide (P4') may also be, for example, referred to as follows:

(P4') a 9- to 50-mer oligonucleotide that is composed of a nucleotide sequence complementary to a nucleotide sequence including 229th to 237th nucleotides in SEQ ID NO: 2 and has a nucleotide complementary to the 237th nucleotide in its 5' end region.

The oligonucleotide (P4') is complementary to a sense strand of BRAF gene, and a polymorphism may be checked through hybridization of the oligonucleotide with the sense strand. In the oligonucleotide (P4'), the nucleotide (w) complementary to a nucleotide (w) of the detection target site in the sense strand is represented by (w) that is a or t.

The oligonucleotide (P4') has a nucleotide complementary to the 237th nucleotide in its 5' end region, preferably at a position of the 1st to 4th nucleotides from the 5' end, more preferably at a position of the 1st to 3rd nucleotides from the same, and particularly preferably at a position of the 2nd nucleotide from the same or the nucleotide at the 5' end.

The probe for BRAF may be, for example, a probe that includes or is composed of the oligonucleotide.

The probe for BRAF preferably is, for example, a labeled probe having a labeling substance. The labeling substance is the same as mentioned above.

The oligonucleotide (P4) preferably has the labeling substance in its 3' end region. Specifically, for example, the labeling substance is located preferably at a position of the 1st the 4th nucleotides from the 3' end, more preferably at a position of the 1st to 3rd nucleotides from the same, and particularly preferably at a position of the 2nd nucleotide from the same or the nucleotide at the 3' end. In the oligonucleotide (P4), for example, it is preferred that any of the 234th to 240th nucleotides has the labeling substance, and it is more preferred that the 237th nucleotide has the labeling substance, for example.

The oligonucleotides (P4') preferably has the labeling substance in its 5' end region. Specifically, for example, the labeling substance is located preferably at a position of the 1st the 4th nucleotides from the 5' end, more preferably at a position of the 1st to 3rd nucleotides from the same, and particularly preferably at a position of the 2nd nucleotide from the same or the nucleotide at the 5' end. In the oligonucleotide (P4'), for example, it is preferred that the nucleotide complementary to any of the 234th to 240th nucleotides has the labeling substance, and it is more preferred that the nucleotide complementary to the 237th nucleotide has the labeling substance, for example.

In the present invention, the combination of the probe for K-ras and the probe for BRAF is not particularly limited, and may be, for example, a combination of a wild-type probe for K-ras including an oligonucleotide of SEQ ID NOs: 7 to 10, 30, and 31 and a mutant-type probe for BRAF including an oligonucleotide of SEQ ID NOs: 27 and 36.

When two or more types of the probes are added to a single reaction system, it is preferable that the respective probes are labeled with labeling substances that are detected under different detection conditions. With this configuration, two or more types of polymorphisms may be detected easily using the same reaction system by merely changing the detection condition.

Specifically, it is preferred that the step (A) is a step of, while changing a temperature of a reaction system containing the test nucleic acid for detecting a polymorphism, the probe for K-ras, and the probe for BRAF, measuring a signal value indicating a melting state of a hybrid between the test nucleic acid and each of the probes. The probe for BRAF is, for example, the same as mentioned above.

In the present invention, the test nucleic acid may further be subjected to, as mentioned above, a step of producing an amplification product from the template nucleic acid, i.e., the step (X). In the production of the amplification product from the template nucleic acid, it is preferable to use a primer for amplifying a sequence including a detection target polymorphism in the BRAF gene (hereinafter also referred to as a "primer for BRAF") in addition to the primer for K-ras, for example. That is, it is preferred that an amplification product is produced using a primer for amplifying a region including the 229th nucleotide in the nucleotide sequence of SEQ ID NO: 2. The sequence of the primer is not particularly limited as long as a detection target sequence including the detection target site may be amplified, for example. The sequence of the primer may be set as appropriate by a conventionally known method depending on the detection target sequence, sequences in the vicinity thereof, and the like. The length of the primer is not particularly limited and may be any of the above-mentioned lengths. The primer for BRAF may be used in combination when the primer for K-ras is used, for example.

As the primer for BRAF, for example, either one of a forward primer (F primer) for amplifying the sense strand of the gene and a reverse primer (R primer) for amplifying the antisense strand of the gene may be used. It is preferable to use a primer set including a pair composed of these primers. Examples of the F primer and the R primer are shown below. It is to be noted that they are merely illustrative and by no means limit the present invention. The primer for BRAF is, for example, preferably a combination of a primer of SEQ ID NO: 38 and a primer of SEQ ID NO: 39.

```
(Primer for BRAF)
F primer
                                      (SEQ ID NO: 20)
5'-cctttacttactacacctcagatatat-3'

F3 primer
                                      (SEQ ID NO: 38)
5'-tgcttgctctgataggaaaatgagatctac-3'

R primer
                                      (SEQ ID NO: 21)
5'-acaactgttcaaactgatgggac-3'

R5 primer
                                      (SEQ ID NO: 39)
5'-aaactgatgggacccactccat-3'
```

The proportions of the probe for BRAF and the primer for BRAF are not particularly limited, and may be the same as those of the probe for K-ras and the primer for K-ras, for example.

<Reagent for Detecting Polymorphism>

The reagent of the present invention is a reagent for detecting a polymorphism in a disease-related gene, containing the probe of the present invention. The reagent of the present invention is characterized in that it contains the above-described probe of the present invention, and the other configurations and conditions are by no means limited. The reagent of the present invention may also be referred to as a probe kit for use in the detection of the polymorphism in the K-ras gene, for example.

The reagent may contain one type of the probe or two or more types of the probes, for example. Specifically, the reagent may contain either one type of a wild-type probe for K-ras and a mutant-type probe for K-ras or two or more types of them.

The reagent of the present invention may further contain a primer or a primer set for amplifying a region including the detection target site in the K-ras gene. Examples of the primer include those mentioned above.

The reagent of the present invention may further contain a primer or a primer set for amplifying a region including the detection target site in the BRAF gene. Examples of the primer include those mentioned above.

The reagent of the present invention further may contain components necessary for the nucleic acid amplification reaction, for example. Specific examples of such components include: polymerases such as DNA polymerases; nucleoside triphosphate; buffer solutions; and various kinds of catalysts. The reagent of the present invention may be referred to as a reagent kit for detection and may further include instructions for use.

Next, the examples of the present invention are described. The present invention is, however, by no means limited by the following examples.

EXAMPLES

Example 1

In the present example, polymorphisms in K-ras genes were detected by carrying out Tm analysis in the presence of a wild-type oligonucleotide or a mutant-type oligonucleotide.

As partial sequences of the K-ras genes, an oligonucleotide (SEQ ID NO: 22) having wild-type codons 12 to 13 and oligonucleotides (SEQ ID NOs: 23 to 26) each having a mutant-type codon 12 or 13 were prepared. In each of SEQ ID NOs 22 to 26, the underlined part corresponds to a sequence of codons 12 to 13, and the nucleotide indicated with a capital letter shows a mutant-type polymorphism.

```
WT
                                                          (SEQ ID NO: 22)
5'-aacttgtggtagttggagctggtggcgtaggcaagagtgccttgacgata-3' c12-TGT
                                                          (SEQ ID NO: 23)
5'-aacttgtggtagttggagctTgtggcgtaggcaagagtgccttgacgata-3'
```

-continued c12-GAT
(SEQ ID NO: 24)
5'-aacttgtggtagttggagctgAtggcgtaggcaagagtgccttgacgata-3' c13-GAC
(SEQ ID NO: 25)
5'-aacttgtggtagttggagctggtgAcgtaggcaagagtgccttgacgata-3' c12-AAT
(SEQ ID NO: 26)
5'-aacttgtggtagttggagctAAtggcgtaggcaagagtgccttgacgata-3'

The concentrations of the respective oligonucleotides were adjusted to 10 µmol/l, thus providing reaction solutions shown in Table 2 below. Each of the reaction solutions was subjected to Tm analysis using a fully-automated SNPs analyzer (I-DENSY produced by ARKRAY, Inc.). The Tm analysis was carried out by treating the reaction solutions at 95° C. for 1 second and at 40° C. for 60 seconds, then heating it from 40° C. to 95° C. at a temperature rising rate of 1° C./3 seconds, and measuring the change in fluorescence intensity over time at a wavelength from 585 to 700 nm.

TABLE 2

(Composition of reaction solution: unit µl)

| | |
|---|---|
| Distilled water | 18.6875 |
| 10 × Universal Buffer *1 | 2.5 |
| 80 v/v % glycerol | 1.5625 |
| 5 µmol/l probe | 1 |
| 10 µmol/l oligonucleotide | 1.25 |
| Total | 25 µl |

*1 manufactured by NIPPON GENE CO., LTD.

As a probe for detecting a polymorphism, the following wild-type probe 1 was used. The probe showed a perfect match with a detection target sequence in the sense strand of the wild-type K-ras gene. In the sequence, a sequence of the underlined nucleotides is complementary to a sequence of wild-type codons 12 to 13. The 5' end of the wild-type probe 1 was labeled with a fluorescent substance, TAMRA, and the 3' end of the same was phosphorylated.

(SEQ ID NO: 7)
5'-(TAMRA)-cctacgccaccagctccaactac-P-3'

Figure 1D:
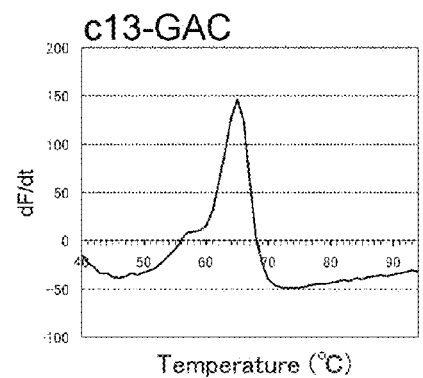
Figure 1B:
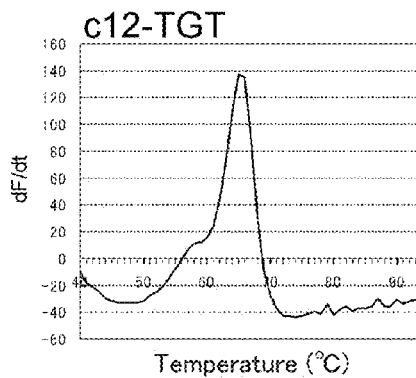
Figure 1E:
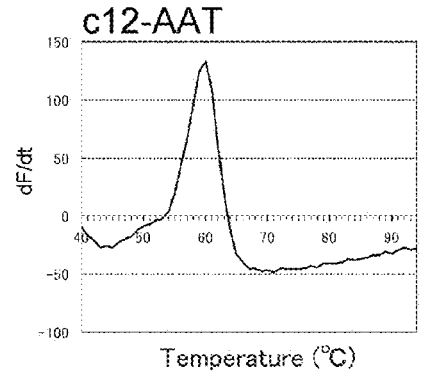
Figure 1C:
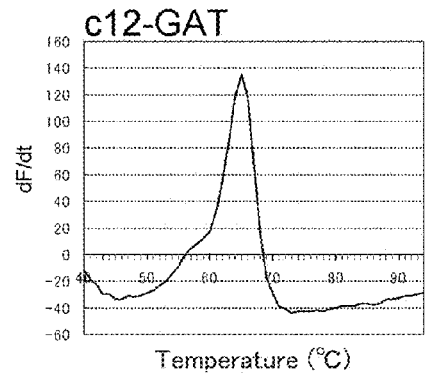

The results thereof are shown in FIGS. 1A to 1E. FIGS. 1A to 1E are graphs showing the Tm analysis results and indicate the change in fluorescence intensity accompanying the temperature rise. FIG. 1A shows the result obtained when the oligonucleotide was WT, FIG. 1B shows the result obtained when the oligonucleotide was c12-TGT, FIG. 1C shows the result obtained when the oligonucleotide was c12-GAT, FIG. 1D shows the result obtained when the oligonucleotide was c13-GAC, and FIG. 1E shows the result obtained when the oligonucleotide was c12-AAT. The horizontal axis indicates a temperature (° C.) at the time of measurement. The vertical axis indicates the change in fluorescence intensity, and the unit thereof is "d amount of change in fluorescence intensity/dt" (dF/dt), being a differential value of the amount of change in fluorescence intensity. The Tm value of the formed hybrid between the probe and the oligonucleotide was as follows: 73° C. when the oligonucleotide was WT; 65° C. when the oligonucleotide was c12-TGT, c12-GAT, or c13-GAC; and 60° C. when the oligonucleotide was c12-AAT.

As can be seen from FIG. 1A, a peak of WT was observed at 73° C. Further, as can be seen from FIGS. 1B to 1D, peaks of c12-TGT, c12-GAT, and c13-GAC in each of which a single nucleotide in codon 12 or 13 was different from a corresponding nucleotide in WT were observed at 65° C. Furthermore, as can be seen from FIG. 1E, a peak of c12-AAT in which two nucleotides in codon 12 were different from corresponding two nucleotides in WT was observed at 60° C. As described above, it was found that, for example, even when the wild-type K-ras gene and a plurality of mutant-type K-ras genes are present together, the wild-type probe according to the present example could distinguish between a wild-type polymorphism and a mutant-type polymorphism and detect them. Moreover, it was found that, the probe according to the present example could distinguish between a polymorphism of single nucleotide mismatch and a polymorphism of double nucleotide mismatch and detect them.

Example 2

In the present example, polymorphisms in K-ras genes were detected by carrying out Tm analysis in the presence of a wild-type plasmid and a mutant-type plasmid.

As partial sequences (from 30th to 349th nucleotides in SEQ ID NO: 1) of the K-ras gene, a wild-type plasmid (WT) obtained through insertion of an oligonucleotide having wild-type codons 12 to 13 and two types of mutant-type plasmids (c12-TGT and c12-GAT) each obtained through insertion of an oligonucleotide having a mutant-type codon 12 and a wild-type codon 13 were prepared. In the wild-type plasmid (WT), a sequence of codons 12 to 13 was "ggtggc". In the mutant-type plasmid (c12-TGT), a sequence of codons 12 to 13 was "Tgtggc", and the nucleotide indicated with a capital letter indicates a mutant-type polymorphism. In the mutant-type plasmid (c12-GAT), a sequence of codons 12 to 13 is "gAtggc", and the nucleotide indicated with a capital letter indicates a mutant-type polymorphism. These plasmids were mixed at predetermined proportions shown below, and thus preparing five types of plasmid samples. Each of these plasmid samples contains $2\times10^4$ copies/µl plasmids.

TABLE 3

(Plasmid sample)

| | Mixing ratio of plasmid | | |
|---|---|---|---|
| | WT | c12-TGT | c12-GAT |
| WT 100% | 100% | 0% | 0% |
| c12-TGT 3% | 97% | 3% | 0% |
| c12-TGT 100% | 0% | 100% | 0% |
| c12-GAT 1% | 99% | 0% | 1% |
| c12-GAT 100% | 0% | 0% | 100% |

25 μl of each of PCR reaction solutions shown in Table 4 below was subjected to PCR and Tm analysis using a fully-automated SNPs analyzer (I-DENSY produced by ARKRAY, Inc.). The PCR was carried out as follows. A treatment at 95° C. for 60 seconds was conducted, and then a cycle of a treatment at 95° C. for 5 seconds and at 64° C. for 15 seconds was repeated a total of 50 cycles. Subsequently, the Tm analysis was conducted under the same conditions as in Example 1.

TABLE 4

(Composition of PCR reaction solution: unit μl)

| Distilled water | 15.97 |
| --- | --- |
| 10 × Universal Buffer*[1] | 2.5 |
| 80 v/v % glycerol | 0.78 |
| 2.5 mmol/l dNTP | 2 |
| 5 μmol/l probe | 1 |
| 100 μmol/l F1 primer | 0.9 |
| 100 μmol/l R-WT primer | 0.05 |
| 100 μmol/l R-c12-XGT primer | 0.15 |
| 100 μmol/l R-c12-GXT primer | 0.15 |
| 20 w/v % BSA | 0.25 |
| 5 U/μl Gene Taq FP*[2] | 0.25 |
| Plasmid sample | 1 |
| Total | 25 μl |

*[2]manufactured by NIPPON GENE CO., LTD.

Sequences of the F primer and various R primers are shown below. In the sequence of R-c12-XGT, the underlined part corresponds to a sequence of codons 12 to 13. In the sequence of R-c12-GXT, the underlined part corresponds to a sequence of two nucleotides from the 5' end of codon 12 and codon 13. Each of R-c12-XGT and R-c12-GXT is a mixture (degenerate primer) of three types of oligonucleotides in which D is t, g, or a.

```
F1 primer
                                        (SEQ ID NO: 11)
5'-accttatgtgtgacatgttctaatatagtcacattttc-3'

R-WT primer
                                        (SEQ ID NO: 13)
5'-ctcttgcctacgccacc-3'

R-c12-XGT
                                        (SEQ ID NO: 14)
5'-cactcttgcctacgccacD-3'
D = t, g, or a R-c12-GXT
                                        (SEQ ID NO: 15)
5'-gcactcttgcctacgccaD-3'
D = t, g, or a
```

As a probe for detecting a polymorphism, the following wild-type probe 2 was used. The probe showed a perfect match with a detection target sequence in the sense strand of the wild-type K-ras gene. In the sequence, a sequence of the underlined nucleotides is complementary to a sequence of wild-type codons 12 to 13. The 5' end of the wild-type probe 2 was labeled with a fluorescent dye, TAMRA, and the 3' end of the same was phosphorylated.

```
                                        (SEQ ID NO: 8)
5'-(TAMRA)-cctgcctacgccaccagctccaactac-P-3'
```

Figure 2A:
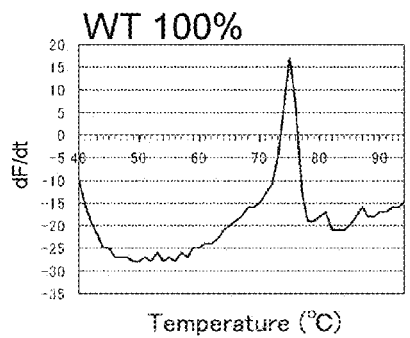
FIGS. 2A to 2E are graphs illustrating the results of Tm analysis with respect to the respective reaction solutions, each containing a wild-type plasmid and a mutant-type plasmid in Example 2 of the present invention.
Figure 2D:
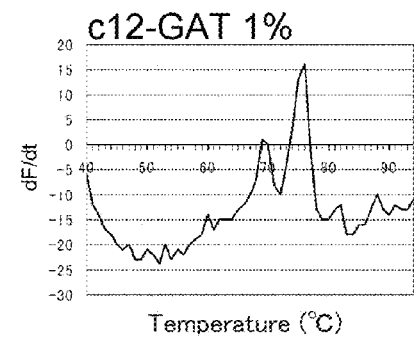
Figure 2B:
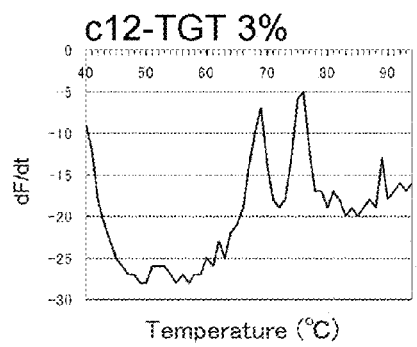
Figure 2E:
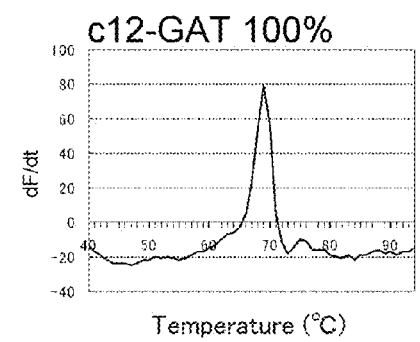
Figure 2C:
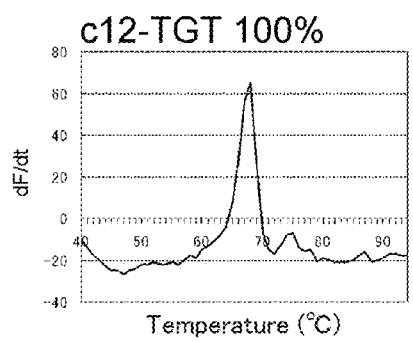

The results thereof are shown in FIGS. 2A to 2E. FIGS. 2A to 2E are graphs showing the Tm analysis results and indicate the change in fluorescence intensity accompanying the temperature rise. FIG. 2A shows the result obtained when the plasmid sample was WT 100%, FIG. 2B shows the result obtained when the plasmid sample was c12-TGT 3%, FIG. 2C shows the result obtained when the plasmid sample was c12-TGT 100%, FIG. 2D shows the result obtained when the plasmid sample was c12-GAT 1%, and FIG. 2E shows the result obtained when the plasmid sample was c12-GAT 100%. In each of FIGS. 2A to 2E, the horizontal axis indicates a temperature (° C.) at the time of measurement, and the vertical axis indicates the change in fluorescence intensity, and the unit thereof is "d amount of change in fluorescence intensity/dt" (dF/dt), being a differential value of the amount of change in fluorescence intensity. The Tm value of the formed hybrid between the probe and the plasmid was as follows: 75° C. when the plasmid was WT; 68° C. when the plasmid was c12-TGT; and 69° C. when the plasmid was c12-GAT.

As can be seen from FIG. 2A, when the plasmid sample was WT 100%, a peak was observed only at the Tm value of WT. As can be seen from FIG. 2C, when the plasmid sample was c12-TGT 100%, a peak was observed only at the Tm value of c12-TGT. As can be seen from FIG. 2E, when the plasmid sample was c12-GAT 100%, a peak was observed only at the Tm value of c12-GAT. In contest, when the plasmid sample was a mixed sample of the wild-type plasmid and the mutant-type plasmid, peaks were observed at two Tm values. That is, as can be seen from FIG. 2B, when the plasmid sample was c12-TGT 3%, peaks were observed both at the neighborhood of the Tm value of WT and at the neighborhood of the Tm value of c12-TGT. Furthermore, as can be seen from FIG. 2D, when the plasmid sample was c12-GAT 1%, peaks were observed both at the neighborhoods of the Tm values of WT and c12-GAT. As described above, it was found that, even when a wild-type polymorphism and a small amount of a mutant-type polymorphism are present together, they can be distinguished from each other and detected using the wild-type probe according to the present example, the wild-type F primer, the wild-type R primer, and the mutant-type R primer.

Example 3

In the present example, polymorphisms in K-ras genes were detected by carrying out Tm analysis in the presence of a wild-type plasmid and a mutant-type plasmid.

As partial sequences (from 30th to 349th nucleotides in SEQ ID NO: 1) of the K-ras gene, a wild-type plasmid (WT) obtained through insertion of an oligonucleotide having wild-type codons 12 to 13 and a mutant-type plasmid (c13-GAC) obtained through insertion of an oligonucleotide having a wild-type codon 12 and a mutant-type codon 13 were prepared. The wild-type plasmid (WT) is the same as that used in Example 2. In the mutant-type plasmid (c13-GAC), a sequence of codons 12 to 13 was "ggtgAc", and the nucleotide indicated with a capital letter indicates a mutant-type polymorphism. These plasmids were mixed at predetermined ratios shown below, and thus preparing three types of plasmid samples. Each of these plasmid samples contains $2 \times 10^4$ copies/μl plasmid.

TABLE 5

(Plasmid sample)

| | Mixing ratio of plasmid | |
|---|---|---|
| | WT | c13-GAC |
| WT 100% | 100% | 0% |
| c13-GAC 3% | 97% | 3% |
| c13-GAC 100% | 0% | 100% |

PCR and Tm analysis were carried out in the same manner as in Example 2 except that 25 μl of each of PCT reaction solutions shown in Table 6 below was used.

TABLE 6

(Composition of PCR reaction solution: unit μl)

| Distilled water | 16.82 |
|---|---|
| 10 × Universal Buffer*[1] | 2.5 |
| 80 v/v % glycerol | 0.78 |
| 2.5 mmol/l dNTP | 2 |
| 5 μmol/l polymorphism detection probe | 1 |
| 100 μmol/l F1 primer | 0.375 |
| 100 μmol/l R-WT primer | 0.05 |
| 100 μmol/l R-c13-TGC primer | 0.05 |
| 100 μmol/l R-c13-GAC primer | 0.05 |
| 20 w/v % BSA | 0.25 |
| 5 U/μl Gene Taq FP*[2] | 0.125 |
| Plasmid sample | 1 |
| Total | 25 μl |

As the F1 primer, the same primer as used in Example 2 was used. The sequences of the various R primers are shown below.

```
R-WT primer
                              (SEQ ID NO: 13)
5'-ctcttgcctacgccacc-3'

R-c13-TGC primer
                              (SEQ ID NO: 16)
5'-caaggcactcttgcctacgca-3'

R-c13-GAC primer
                              (SEQ ID NO: 17)
5'-tcaaggcactcttgcctacgt-3'
```

As a probe for detecting a polymorphism, the following wild-type probe 3 was used. The probe showed a perfect match with a detection target sequence in the sense strand of the wild-type K-ras gene. In the sequence, a sequence of the underlined nucleotides is complementary to a sequence of wild-type codons 12 to 13. The 5' end of the wild-type probe 3 was labeled with a fluorescent dye, TAMRA, and the 3' end of the same was phosphorylated.

```
                                         (SEQ ID NO: 9)
5'-(TAMRA)-cctgcctacgccaccagctccaactacca-P-3'
```

Figure 3A:
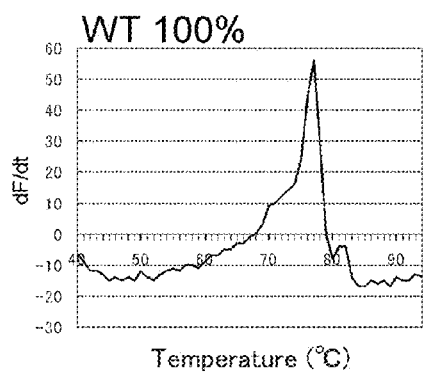
FIGS. 3A to 3C are graphs illustrating the results of Tm analysis with respect to the respective reaction solutions, each containing a wild-type plasmid and a mutant-type plasmid in Example 3 of the present invention.
Figure 3C:
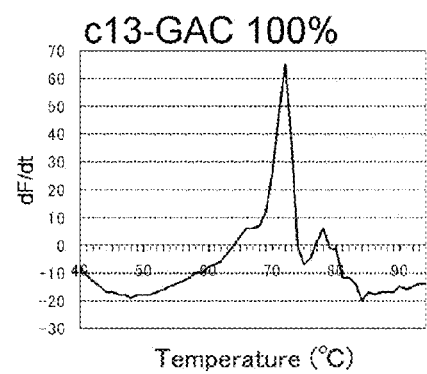
Figure 3B:
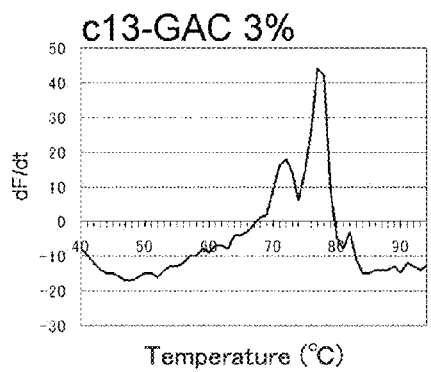

The results thereof are shown in FIG. 3A to 3C. FIG. 3A to 3C are graphs showing the Tm analysis results and indicate the change in fluorescence intensity accompanying the temperature rise. FIG. 3A shows the result obtained when the plasmid sample was WT 100%, FIG. 3B shows the result obtained when the plasmid sample was c13-GAC 3%, and FIG. 3C shows the result obtained when the plasmid sample was c13-GAC 100%. In each of FIGS. 3A to 3C, the horizontal axis indicates a temperature (° C.) at the time of measurement, and the vertical axis indicates the change in fluorescence intensity, and the unit thereof is "d amount of change in fluorescence intensity/dt" (dF/dt), being a differential value of the amount of change in fluorescence intensity. The Tm value of the formed hybrid between the probe and the plasmid was as follows: 77° C. when the plasmid was WT; and 72° C. when the plasmid was c13-GAC.

As can be seen from FIG. 3A, when the plasmid sample was WT 100%, a peak was observed only at the Tm value of WT. As can be seen from FIG. 3C, when the plasmid sample was c13-GAC 100%, a peak was observed only at the Tm value of c13-GAC. In contrast, as can be seen from FIG. 3B, when the plasmid sample was c13-GAC 3% containing the wild-type plasmid and the mutant-type plasmid, peaks were observed both at the Tm value of WT and at the Tm value of c13-GAC. As described above, it was found that, even when a wild-type polymorphism and a small amount of a mutant-type polymorphism are present together, they can be distinguished from each other and detected using the wild-type probe according to the present example, the wild-type F primer, the wild-type R primer, and the mutant-type R primer.

Example 4

In the present example, polymorphisms in K-ras genes and BRAF genes were detected by carrying out Tm analysis in the presence of a wild-type plasmid and a mutant-type plasmid.

As partial sequences (from 30th to 349th nucleotides in SEQ ID NO: 1) of the K-ras gene, kras plasmids obtained through insertion of the respective oligonucleotides having codons 12 to 13 shown in Table 7 below were prepared. The kras plasmid in which codons 12 to 13 are of a wild-type was referred to as a wild-type plasmid (kras-wt). The kras plasmid in which at least one of codons 12 to 13 has a mutant-type polymorphism was referred to as a mutant-type plasmid (kras-mt), and 12 types of "kras-mt 2" to "kras-mt 13" were prepared depending on the respective mutant-type polymorphisms thereof. In codons 12 to 13 in Table 7 below, the nucleotides indicated with capital letters show mutant-type polymorphisms.

Furthermore, as partial sequences (from 51st to 350th nucleotides in SEQ ID NO: 2) of the BRAF gene, braf plasmids obtained through insertion of the respective oligonucleotides each having a nucleotide shown in Table 7 below as the detection site were prepared. The braf plasmid obtained through insertion of the oligonucleotide having a wild-type detection site was referred to as a wild-type plasmid (braf-wt). The braf plasmid obtained through insertion of the oligonucleotide having a mutant-type detection site was referred to as a mutant-type plasmid (braf-mt). Each of the nucleotides in Table 7 below is the 229th nucleotide (w) in the nucleotide sequence of SEQ ID NO: 2. In Table 7, the nucleotide indicated with a capital letter is a mutant-type polymorphism.

TABLE 7

(kras plasmid)

| | codon 12 | codon 13 |
|---|---|---|
| kras-wt | ggt | ggc |
| kras-mt 2 | Agt | ggc |
| kras-mt 3 | Cgt | ggc |
| kras-mt 4 | Tgt | ggc |
| kras-mt 5 | gAt | ggc |
| kras-mt 6 | gCt | ggc |
| kras-mt 7 | gTt | ggc |
| kras-mt 8 | ggt | Tgc |

TABLE 7-continued

| | | |
|---|---|---|
| kras-mt 9 | ggt | gAc |
| kras-mt 10 | AAt | ggc |
| kras-mt 11 | TTt | ggc |
| kras-mt 12 | CTt | ggc |
| kras-mt 13 | Agt | gAc |

(braf plasmid)

| BRAF gene | |
|---|---|
| braf-wt | t |
| braf-mt | A |

The kras plasmids and the braf plasmids were mixed at a predetermined ratios shown below, and thus preparing 14 types of plasmid samples. Each of these plasmid samples contains $1 \times 10^4$ copies/µl of plasmids.

TABLE 8

| Plasmid sample name | Plasmid name | Proportion |
|---|---|---|
| WT 100% | kras-wt | 50.0% |
| | braf-wt | 50.0% |
| kras-mt 2 10% | kras-wt | 45.0% |
| | kras-mt 2 | 5.0% |
| | braf-wt | 50.0% |
| kras-mt 3 10% | kras-wt | 45.0% |
| | kras-mt 3 | 5.0% |
| | braf-wt | 50.0% |
| kras-mt 4 10% | kras-wt | 45.0% |
| | kras-mt 4 | 5.0% |
| | braf-wt | 50.0% |
| kras-mt 5 10% | kras-wt | 45.0% |
| | kras-mt 5 | 5.0% |
| | braf-wt | 50.0% |
| kras-mt 6 10% | kras-wt | 45.0% |
| | kras-mt 6 | 5.0% |
| | braf-wt | 50.0% |
| kras-mt 7 10% | kras-wt | 45.0% |
| | kras-mt 7 | 5.0% |
| | braf-wt | 50.0% |
| kras-mt 8 10% | kras-wt | 45.0% |
| | kras-mt 8 | 5.0% |
| | braf-wt | 50.0% |
| kras-mt 9 10% | kras-wt | 45.0% |
| | kras-mt 9 | 5.0% |
| | braf-wt | 50.0% |
| kras-mt 10 10% | kras-wt | 45.0% |
| | kras-mt 10 | 5.0% |
| | braf-wt | 50.0% |
| kras-mt 11 10% | kras-wt | 45.0% |
| | kras-mt 11 | 5.0% |
| | braf-wt | 50.0% |
| kras-mt 12 10% | kras-wt | 45.0% |
| | kras-mt 12 | 5.0% |
| | braf-wt | 50.0% |
| kras-mt 13 10% | kras-wt | 45.0% |
| | kras-mt 13 | 5.0% |
| | braf-wt | 50.0% |
| braf mt | kras-wt | 50.0% |
| | braf-wt | 45.0% |
| | braf-mt | 5.0% |

50 µl of each of PCR reaction solutions shown in Table 9 below was subjected to PCR and Tm analysis using a fully-automated SNPs analyzer (I-DENSY produced by ARKRAY, Inc.). The PCR was carried out as follows. A treatment at 95° C. for 30 seconds was conducted, and then a cycle of a treatment at 95° C. for 1 second and at 58° C. for 15 seconds was repeated a total of 50 cycles. Subsequently, the Tm analysis was carried out by treating the reaction solutions at 95° C. for 1 second and at 40° C. for 60 seconds, then heating it from 40° C. to 85° C. at a temperature rising rate of 1° C./3 seconds, and measuring the change in fluorescence intensity over time at a wavelength from 520 to 555 nm (BODIPY FL) and from 585 to 700 nm (TAMRA).

TABLE 9

| (Composition of PCR reaction solution: unit µl) | |
|---|---|
| Distilled water | 35.71 |
| 1 mol/l Tris-HCl (pH 8.6) | 1.25 |
| 20 w/v % BSA | 0.5 |
| 10 w/v % NaN$_3$ | 0.23 |
| 80 v/v % glycerol | 1.56 |
| 100 mmol/l MgCl$_2$ | 0.75 |
| 1 mol/l KCl | 1.25 |
| 10 mmol/l dNTP | 1 |
| 100 µmol/l F2 primer for K-ras | 0.5 |
| 100 µmol/l R2 primer for K-ras | 0.25 |
| 5 µmol/l probe for K-ras | 2 |
| 100 µmol/l F primer for BRAF | 0.25 |
| 100 µmol/l R primer for BRAF | 0.5 |
| 5 µmol/l probe for BRAF | 2 |
| 5 U/µl Gene Taq FP*[2] | 0.25 |
| Plasmid sample | 2 |
| Total | 50 µl |

Sequences of the primers for K-ras and the primers for BRAF are shown below.

```
(Primer for K-ras)
F2 primer
                                          (SEQ ID NO: 12)
5'-aaggcctgctgaaaatgactg-3'

R2 primer
                                          (SEQ ID NO: 18)
5'-ggtcctgcaccagtaatatgca-3'

(Primer for BRAF)
F primer
                                          (SEQ ID NO: 20)
5'-cctttacttactacacctcagatatat-3'

R primer
                                          (SEQ ID NO: 21)
5'-acaactgttcaaactgatgggac-3'
```

Sequences of the probe for Kras and the probe for BRAF are shown below. The probe for K-ras has a sequence that may hybridize to the sense strand of the K-ras gene, and in the sequence, the nucleotides indicated with capital letters are complementary to the 220th to 225th nucleotides (nntkrc) in SEQ ID NO: 1. The 5' end of the probe for K-ras was labeled with a fluorescent substance, BODIPY FL, and the 3' end of the same was phosphorylated. The probe for BRAF has a sequence that may hybridize to the antisense strand of the BRAF gene, and in the sequence, the nucleotide indicated with a capital letter corresponds to the 229th nucleotide (w) in SEQ ID NO: 2. The 3' end of the probe for BRAF was labeled with a fluorescent substance, TAMRA.

```
(Probe for K-ras)
                                          (SEQ ID NO: 10)
5'-(BODIPY FL)-ctcttgcctacGCCACCagctccaact-P-3'

(Probe for BRAF)
                                          (SEQ ID NO: 27)
5'-ctagctacagAgaaatctc-(TAMRA)-3'
```

Figure 4:
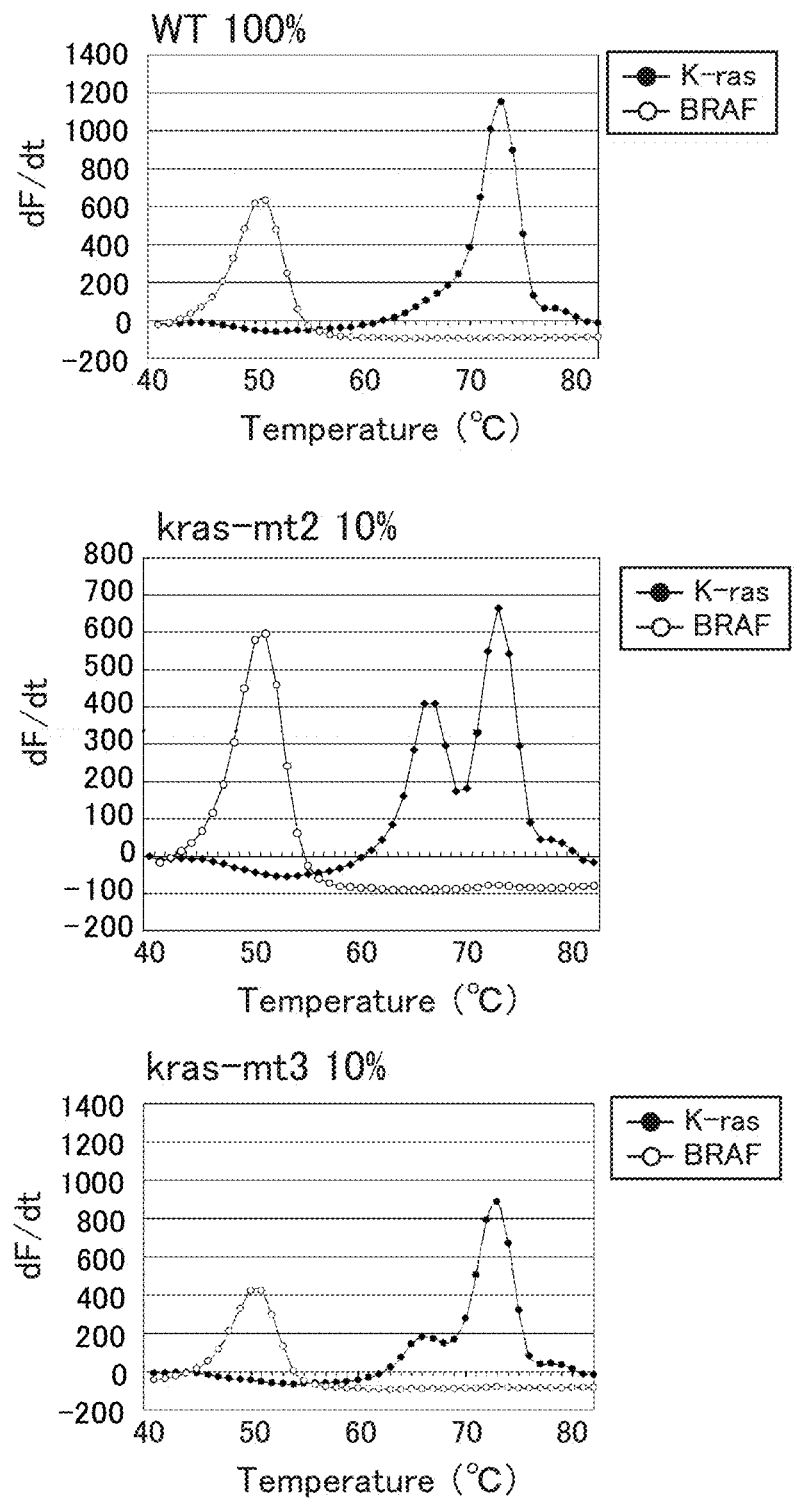
FIG. 4 shows graphs illustrating the results of Tm analysis with respect to the respective reaction solutions, each containing a wild-type plasmid and a mutant-type plasmid in Example 4 of the present invention.
Figure 5:
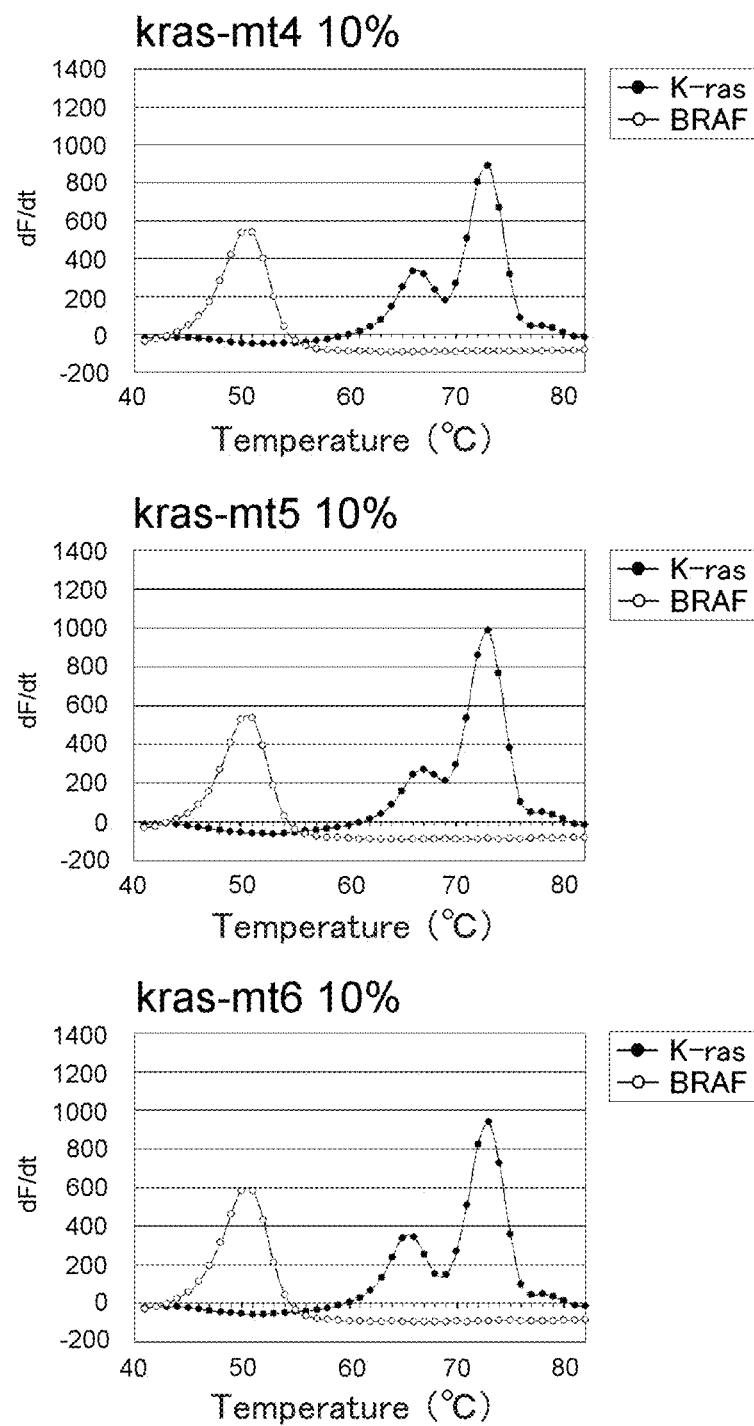
FIG. 5 shows other graphs illustrating the results of Tm analysis with respect to the respective reaction solutions, each containing a wild-type plasmid and a mutant-type plasmid in Example 4 of the present invention.
Figure 6:
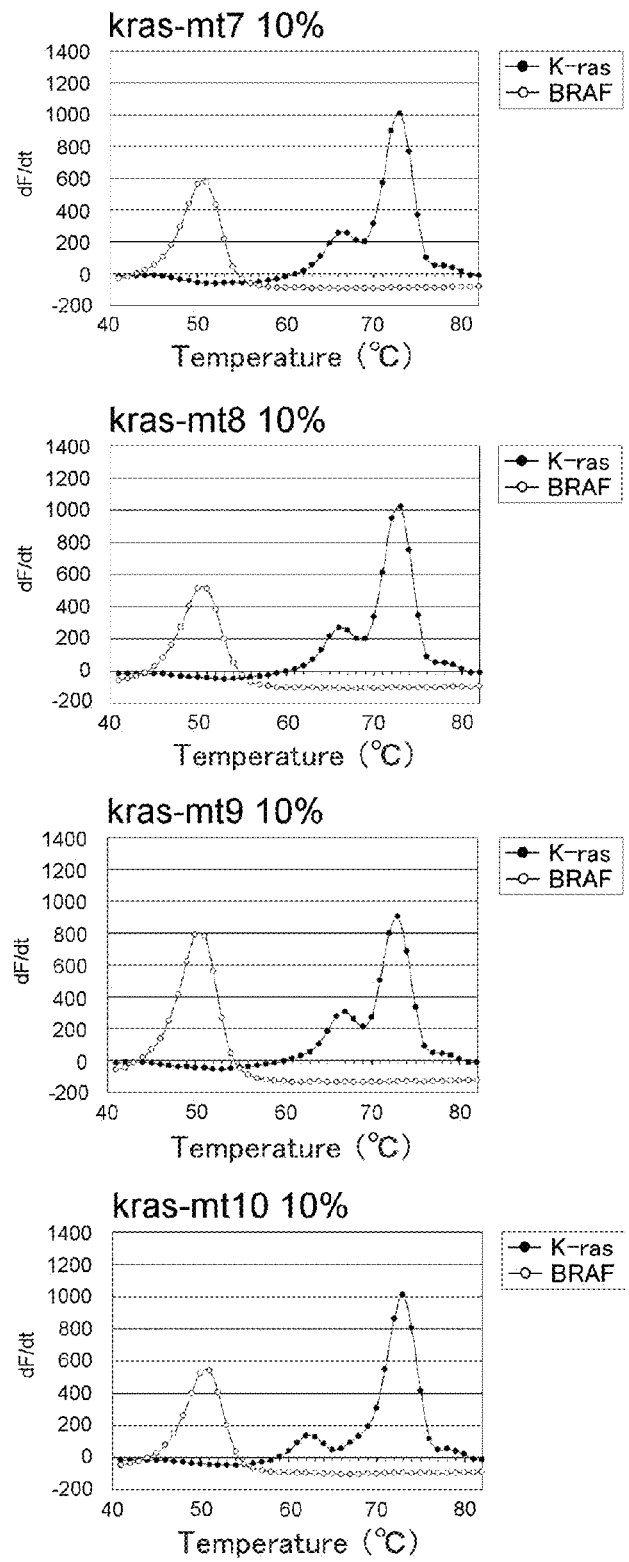
FIG. 6 shows other graphs illustrating the results of Tm analysis with respect to the respective reaction solutions, each containing a wild-type plasmid and a mutant-type plasmid in Example 4 of the present invention.
Figure 7:
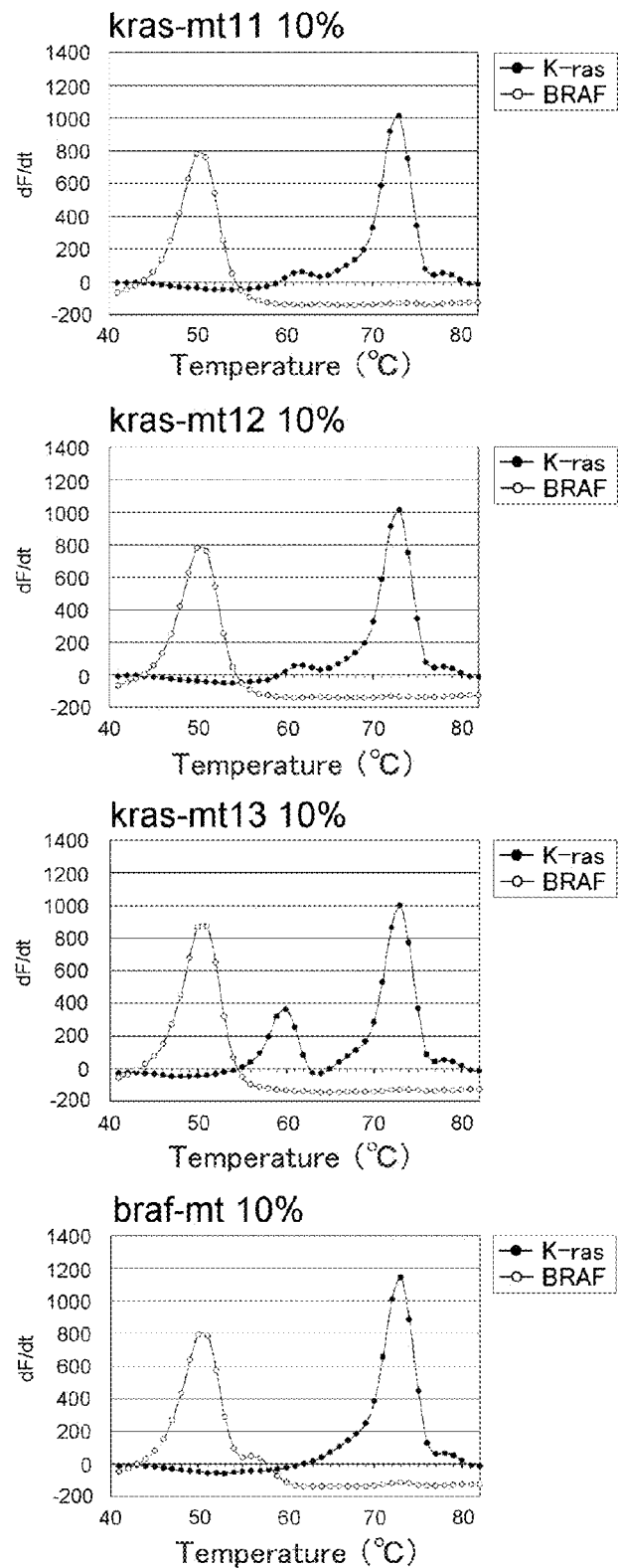
FIG. 7 shows graphs illustrating the results of Tm analysis with respect to the respective reaction solutions, each containing a wild-type plasmid and a mutant-type plasmid in Example 4 of the present invention.

The results thereof are shown in FIGS. 4 to 7. FIGS. 4 to 7 show graphs showing the Tm analysis results and indicate the change in fluorescence intensity accompanying the temperature rise. FIG. 4 shows the results obtained when the respective plasmid samples were WT 100%, kras-mt 2 10%, and kras-mt 3 10%. FIG. 5 shows the results obtained when the respective plasmid samples were kras-mt 4 10%, kras-mt 5 10%, and kras-mt 6 10%. FIG. 6 shows the results obtained when the respective plasmid samples were kras-mt 7 10%, kras-mt 8 10%, kras-mt 9 10%, and kras-mt 10 10%. FIG. 7 shows the results obtained when the respective plasmid samples were kras-mt 11 10%, kras-mt 12 10%, kras-mt13 10%, and braf-mt 10%. In each of FIGS. 4 to 7, the horizontal axis indicates a temperature (° C.) at the time of measurement, and the vertical axis indicates the change in fluorescence intensity, and the unit thereof is "d amount of change in fluorescence intensity/dt" (dF/dt), being a differential value of the amount of change in fluorescence intensity. The Tm value of the formed hybrid between the probe for K-ras and the plasmid was as follows: 73° C. when the plasmid was kras-wt; 67° C. when the plasmid was kras-mt 2; 66° C. when the plasmid was kras-mt 3; 67° C. when the plasmid was kras-mt 4; 67° C. when the plasmid was kras-mt 5; 66° C. when the plasmid was kras-mt 6; 67° C. when the plasmid was kras-mt 7; 66° C. when the plasmid was kras-mt 8; 67° C. when the plasmid was kras-mt 9; 62° C. when the plasmid was kras-mt 10; 62° C. when the plasmid was kras-mt 11; 62° C. when the plasmid was kras-mt 12; and 60° C. when the plasmid was kras-mt 13. The Tm value of the formed hybrid between the probe for BRAF and the plasmid was as follows: 51° C. when the plasmid was braf-wt; and 57° C. when the plasmid was braf-mt.

As can be seen from FIG. 4, when the plasmid sample was WT 100%, peaks were observed only at the Tm value of kras-wt and at the Tm value of braf-wt. In contrast, as can be seen from FIGS. 4 to 7, when the plasmid sample was any of the various plasmid samples each containing a wild-type plasmid and a mutant-type plasmid, a total of three peaks at the neighborhoods of the Tm values of kras-wt, kras-mt, and braf-wt or a total of three peaks at the neighborhoods of the Tm values of kras-wt, braf-wt, and braf-mt were observed. As described above, it was found that, a polymorphism(s) in the K-ras gene and the BRAF gene can be detected using the probes for K-ras and the probes for BRAF of the present example together in one reaction solution.

Example 5

In the present example, polymorphisms in the K-ras gene and the BRAF gene were detected by carrying out Tm analysis with respect to a DNA extract obtained from a clinical specimen of paraffin-embedded section.

The DNA extract was obtained from the clinical specimen of paraffin-embedded section using the DNA extraction kit (trade name: TaKaRaDEXPAT (registered trademark), product code: 9091, produced by Takara Bio Inc).

50 µl of each of PCR reaction solutions shown in Table 10 below was subjected to PCR and Tm analysis using a fully-automated SNPs analyzer (I-DENSY produced by ARKRAY, Inc.). The PCR was carried out as follows. A treatment at 95° C. for 60 seconds was conducted, and then a cycle of a treatment at 95° C. for 1 second and at 62° C. for 15 seconds was repeated a total of 50 cycles. Subsequently, the Tm analysis was carried out by treating the reaction solutions at 95° C. for 1 second and at 40° C. for 60 seconds, then heating it from 40° C. to 85° C. at a temperature rising rate of 1° C./3 seconds, and measuring the change in fluorescence intensity over time at a wavelength from 520 to 555 nm (BODIPY FL) and from 585 to 700 nm (TAMRA).

TABLE 10

| (Composition of PCR reaction solution: unit µl) | |
|---|---|
| Distilled water | 31.96 |
| 1 mol/l Tris-HCl (pH 8.6) | 1.25 |
| 20 w/v % BSA | 0.5 |
| 10 w/v % NaN$_3$ | 0.23 |
| 80 v/v % glycerol | 1.56 |
| 100 mmol/l MgCl$_2$ | 0.75 |
| 1 mol/l KCl | 1.25 |
| 10 mmol/l dNTP | 1 |
| 100 µmol/l F2 primer for K-ras | 0.5 |
| 100 µmol/l R2 primer for K-ras | 0.25 |
| 5 µmol/l probe for K-ras | 2 |
| 100 µmol/l F3 primer for BRAF | 0.25 |
| 100 µmol/l R5 primer for BRAF | 0.5 |
| 5 µmol/l probe for BRAF | 2 |
| 0.94 U/µl Gene Taq FP*[2] | 2 |
| DNA extract | 4 |
| Total | 50 |

As the primers for K-ras, the same primers as used in Example 4 were used. The sequences of the primers for BRAF are shown below.

```
(Primer for BRAF)
F3 primer
                               (SEQ ID NO: 38)
5'-tgcttgctctgataggaaaatgagatctac-3'

R5 primer
                               (SEQ ID NO: 39)
5'-aaactgatgggacccactccat-3'
```

As the probe for K-ras, the same probe used in Example 4 was used. The sequence of the probe for BRAF is shown below. In the sequence, the nucleotide indicated with a capital letter corresponds to the 229th nucleotide (w) in SEQ ID NO: 2. The 3' end of the probe for BRAF was labeled with a fluorescent substance, TAMRA.

```
(Probe for BRAF)
                               (SEQ ID NO: 36)
5'-gctacagAgaaatetc-(TAMRA)-3'
```

Figure 8A:
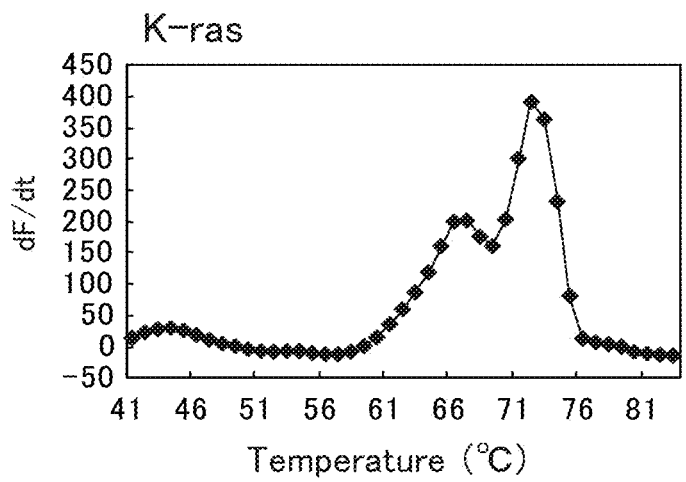
FIGS. 8A and 8B are graphs illustrating the results of Tm analysis with respect to a reaction solution containing a DNA extract from a clinical specimen in Example 5 of the present invention.
Figure 8B:
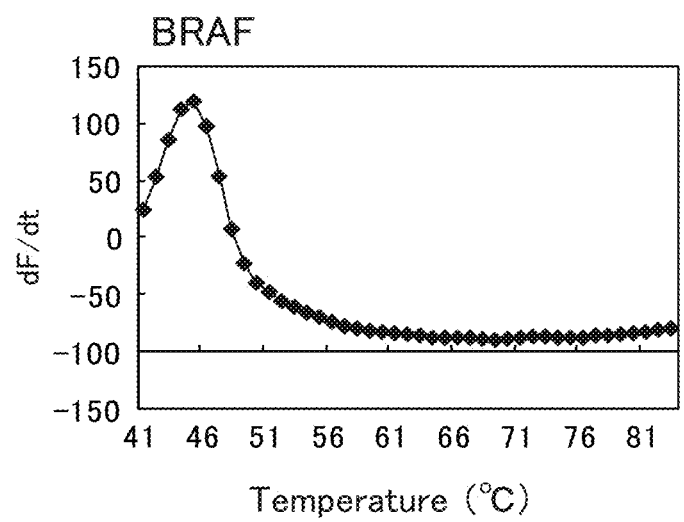

The results thereof are shown in FIGS. 8A and 8B. FIGS. 8A and 8B are graphs showing the Tm analysis results and indicate the change in fluorescence intensity accompanying the temperature rise. FIG. 8A shows the result with respect to the K-ras gene, and FIG. 8B shows the result with respect to the BRAF gene. The horizontal axis indicates a temperature (° C.) at the time of measurement. The vertical axis indicates the change in fluorescence intensity, and the unit thereof is "d amount of change in fluorescence intensity/dt" (dF/dt), being a differential value of the amount of change in fluorescence intensity. The Tm value of the formed hybrid between the probe for K-ras and the K-ras gene of a wild type was about 73° C. The Tm value of the formed hybrid between the probe for BRAF and the BRAF gene was as follows: 52° C. when the BRAF gene is of a wild type; and 45° C. when the BRAF gene is of a mutant type.

As can be seen from FIG. 8A, two peaks were observed with respect to the K-ras gene. Therefore, it was found that the K-ras gene contains a wild-type sequence and a mutant-type sequence. As can be seen from FIG. 8B, a peak was observed only at the Tm value of a wild-type DNA with respect to the BRAF gene. Therefore, it was found that the DNA is of a wild-type. It was expected that the DNA extract collected from the clinical specimen of paraffin-embedded section contained contaminants, or a template DNA was fragmented. However, according to the present example, the peaks with respect to the K-ras gene and the BRAF gene could be detected clearly.

Example 6

In the present example, polymorphisms in K-ras genes were detected by carrying out Tm analysis in the presence of a wild-type plasmid and a mutant-type plasmid.

The kras plasmids were mixed in the same manner as in Example 4 except that the braf plasmids in Table 8 were not contained, and thus preparing plasmid samples. Each of the plasmid samples contains 75 copies/µl of plasmids.

50 µl of each of PCR reaction solutions shown in Table 11 below was subjected to PCR and Tm analysis using a fully-automated SNPs analyzer (I-DENSY produced by ARKRAY, Inc.). The PCR was carried out as follows. A treatment at 95° C. for 60 seconds was conducted, and then a cycle of a treatment at 95° C. for 1 second and at 58° C. for 15 seconds was repeated a total of 50 cycles. Subsequently, the Tm analysis was carried out by treating the reaction solutions at 95° C. for 1 second and at 40° C. for 60 seconds, then heating it from 40° C. to 85° C. at a temperature rising rate of 1° C./3 seconds, and measuring the change in fluorescence intensity over time at a wavelength from 520 to 555 nm (BODIPY FL).

TABLE 11

(Composition of PCR reaction solution: unit µl)

| | |
|---|---|
| Distilled water | 37.285 |
| 1 mol/l Tris-HCl (pH 8.6) | 1.25 |
| 20 w/v % BSA | 0.5 |
| 10 w/v % NaN$_3$ | 0.23 |
| 80 v/v % glycerol | 1.56 |
| 1 mol/l MgCl$_2$ | 0.075 |
| 1 mol/l KCl | 1.25 |
| 10 mmol/l dNTP | 1 |
| 100 µmol/l F1-LP primer | 0.5 |
| 100 µmol/l R1-LP primer | 0.25 |
| 100 µmol/l probe | 0.1 |
| 0.94 U/µl Gene Taq FP*$^2$ | 2 |
| Plasmid sample | 4 |
| Total | 50 |

Sequences of the F1-LP primer and the R1-LP primer are shown below. The R1-LP primer was a mixture (degenerate primer) of two types of oligonucleotides in which m is c or a.

```
F1-LP primer
                              (SEQ ID NO: 32)
5'-ggtactggtggagtatttgatagtgt-3'

R1-LP primer
                              (SEQ ID NO: 33)
5'-gaattagctgtatcgtmaaggcactc-3'
m = c or a
```

As the probe for detecting a polymorphism, a wild-type probe 6 having the following sequence was used. In the sequence, a sequence of the underlined nucleotides is complementary to a sequence of the wild-type codons 12 to 13. The 5' end of the wild-type probe 6 was labeled with a fluorescent substance, BODIPY FL, and the 3' end of the same was phosphorylated.

Figure 9:
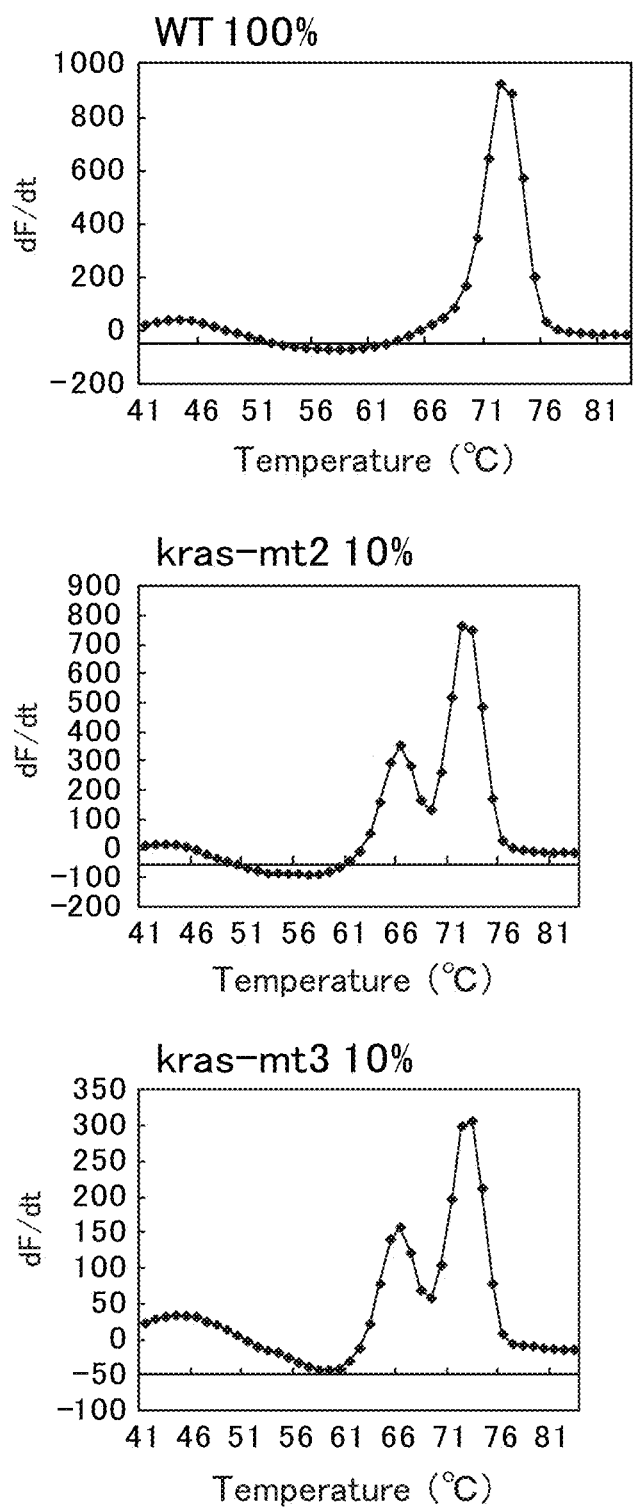
FIG. 9 shows graphs illustrating the results of Tm analysis with respect to the respective reaction solutions, each containing a wild-type plasmid and a mutant-type plasmid in Example 6 of the present invention.
Figure 10:
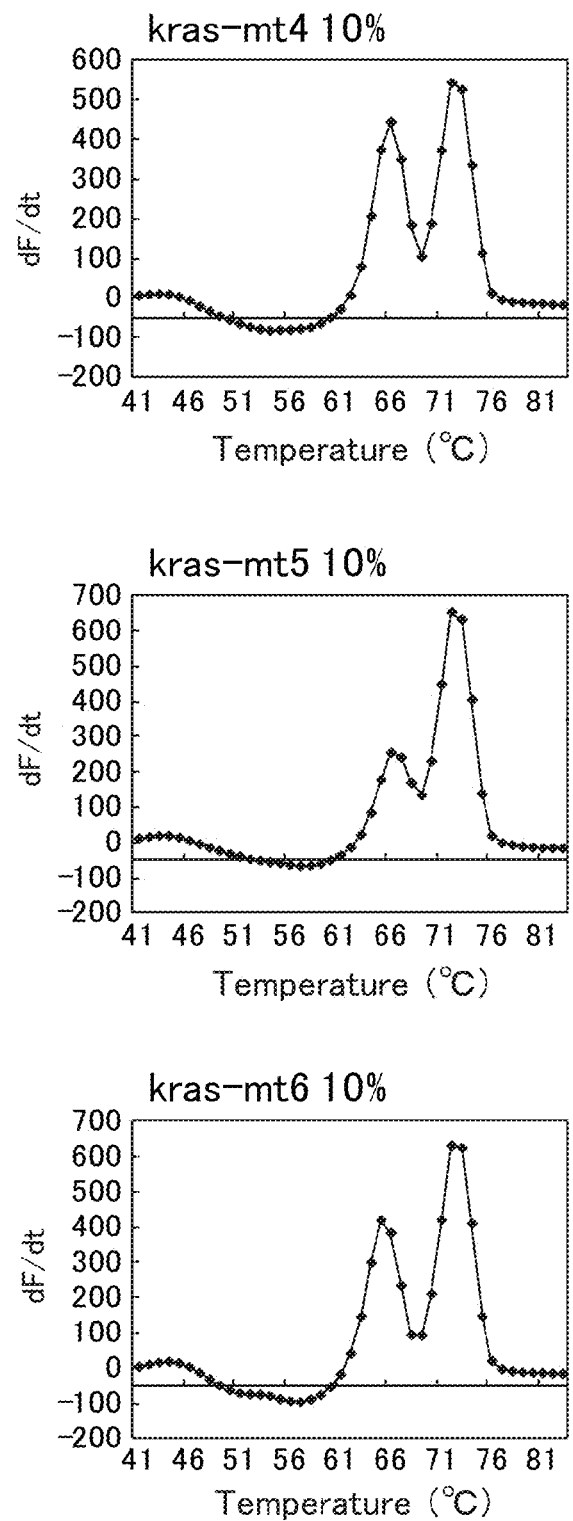
FIG. 10 shows other graphs illustrating the results of Tm analysis with respect to the respective reaction solutions, each containing a wild-type plasmid and a mutant-type plasmid in Example 6 of the present invention.
Figure 11:
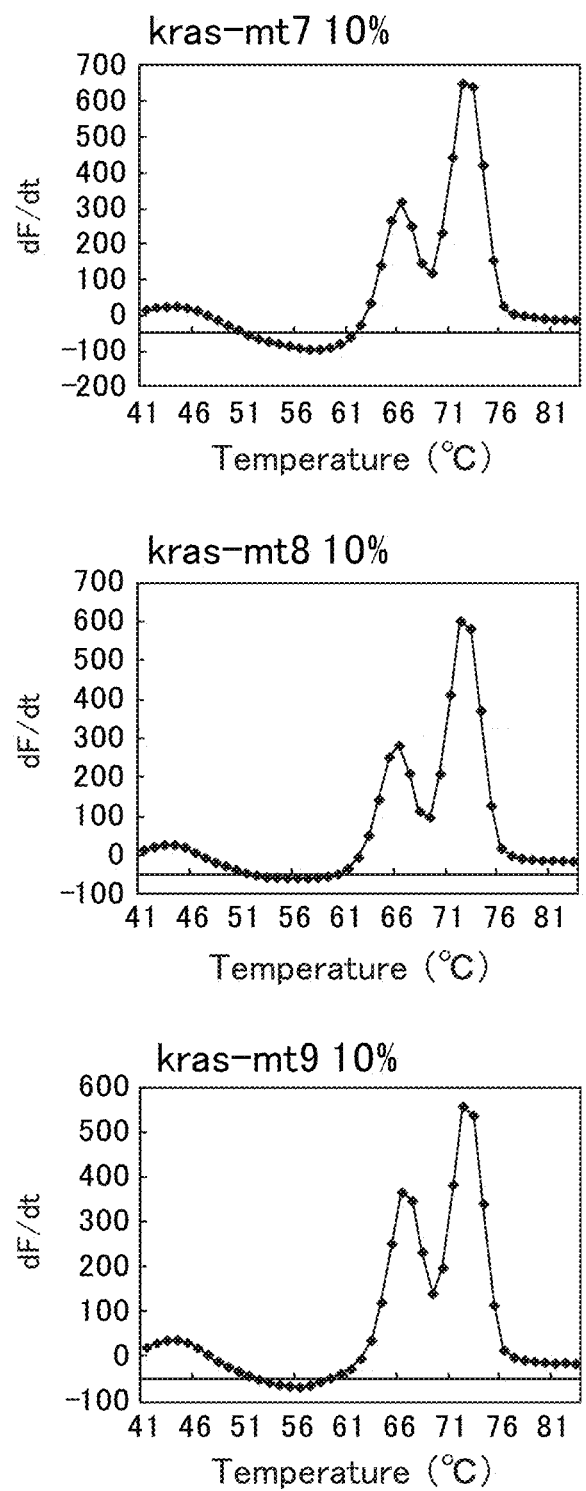
FIG. 11 shows other graphs illustrating the results of Tm analysis with respect to the respective reaction solutions, each containing a wild-type plasmid and a mutant-type plasmid in Example 6 of the present invention.
Figure 12:
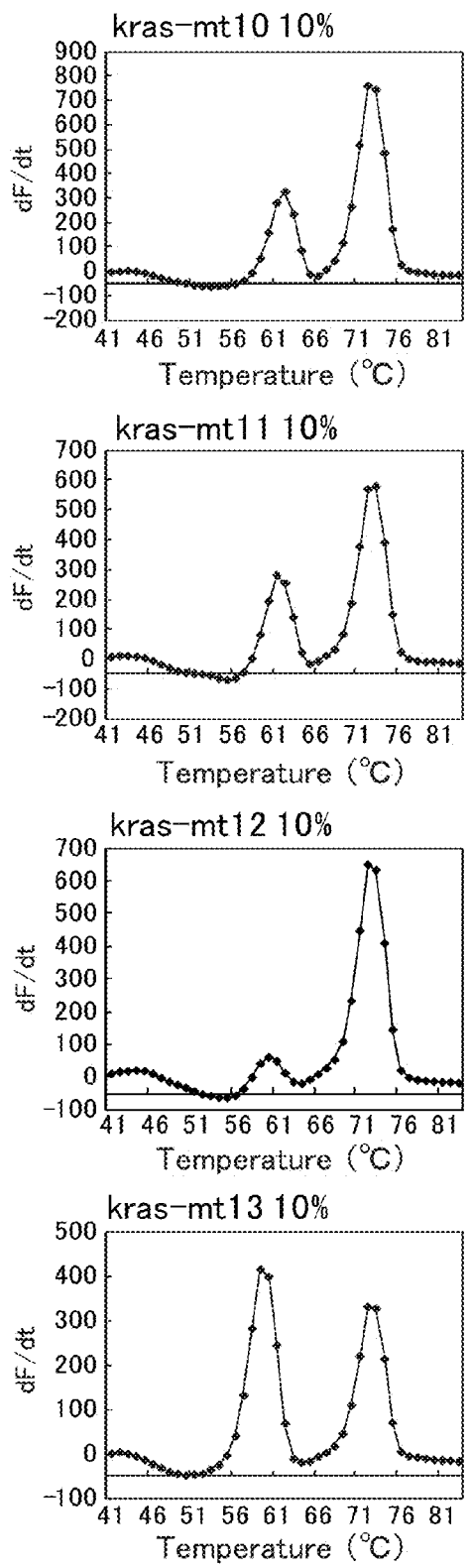
FIG. 12 shows other graphs illustrating the results of Tm analysis with respect to the respective reaction solutions, each containing a wild-type plasmid and a mutant-type plasmid in Example 6 of the present invention.

The results thereof are shown in FIGS. 9 to 12. FIGS. 9 to 12 show graphs showing the Tm analysis results and indicate the change in fluorescence intensity accompanying the temperature rise. FIG. 9 shows the results obtained when the respective plasmid samples were WT 100%, kras-mt 2 10%, and kras-mt 3 10%. FIG. 10 shows the results obtained when the respective plasmid samples were kras-mt 4 10%, kras-mt 5 10%, and kras-mt 6 10%. FIG. 11 shows the results obtained when the respective plasmid samples were kras-mt 7 10%, kras-mt 8 10%, and kras-mt 9 10%. FIG. 12 shows the results obtained when the respective plasmid samples were kras-mt 10 10%, kras-mt 11 10%, kras-mt 12 10%, and kras-mt13 10%. In each of FIGS. 9 to 12, the horizontal axis indicates a temperature (° C.) at the time of measurement, and the vertical axis indicates the change in fluorescence intensity, and the unit thereof is "d amount of change in fluorescence intensity/dt" (dF/dt), being a differential value of the amount of change in fluorescence intensity. The Tm value of the formed hybrid between the probe for K-ras and the plasmid was as follows: 72° C. when the plasmid was kras-wt; 66° C. when the plasmid was kras-mt 2; 66° C. when the plasmid was kras-mt 3; 66° C. when the plasmid was kras-mt 4; 66° C. when the plasmid was kras-mt 5; 65° C. when the plasmid was kras-mt 6; 66° C. when the plasmid was kras-mt 7; 66° C. when the plasmid was kras-mt 8; 66° C. when the plasmid was kras-mt 9; 62° C. when the plasmid was kras-mt 10; 61° C. when the plasmid was kras-mt 11; 60° C. when the plasmid was kras-mt 12; and 59° C. when the plasmid was kras-mt 13.

As can be seen from FIG. 9, when the plasmid sample was WT 100%, a peak was observed only at the Tm value of kras-wt. In contrast, as can be seen from FIGS. 9 to 12, when the plasmid sample was any of the various plasmid samples containing a wild-type plasmid and a mutant-type plasmid, a total of two peaks were observed at the neighborhoods of the Tm values of kras-wt and kras-mt. As described above, it was found that, even when a wild-type polymorphism and a small amount of mutant-type polymorphism are present together, the wild-type probe of the present example could distinguish between the wild-type polymorphism and the mutant-type polymorphism and detect them.

Example 7

In the present example, polymorphisms in K-ras genes were detected by carrying out Tm analysis in the presence of a wild-type plasmid and a mutant-type plasmid. As plasmid samples, the plasmid samples, WT and mt 2 to 9 among the plasmids samples of Example 6 were used.

50 µl of each of PCR reaction solutions shown in Table 12 below was subjected to PCR and Tm analysis using a fully-automated SNPs analyzer (I-DENSY produced by ARKRAY, Inc.), produced by ARKRAY, Inc.). The PCR was carried out as follows. A treatment at 95° C. for 60 seconds was conducted, and then a cycle of a treatment at 95° C. for 1 second and at 57.5° C. for 15 seconds was repeated a total of 50 cycles. Subsequently, the Tm analysis was carried out by treating the reaction solutions at 95° C. for 1 second and at 40° C. for 60 seconds, then heating it from 40° C. to 65° C. at a temperature rising rate of 1° C./3 seconds, and measuring the change in fluorescence intensity over time at a wavelength from 585 to 700 nm (TAMRA).

```
                              (SEQ ID NO: 31)
5'-(BODIPY FL)-ctcttgcctacgccaccagctccaacttgctggctacgc-P-3'
```

TABLE 12

(Composition of PCR reaction solution: unit μl)

| | |
|---|---|
| Distilled water | 33.77 |
| 1 mol/l Tris-HCl (pH 8.6) | 1.25 |
| 20 w/v % BSA | 0.5 |
| 10 w/v % NaN$_3$ | 0.23 |
| 80 v/v % glycerol | 5 |
| 1 mol/l MgCl$_2$ | 0.15 |
| 1 mol/l KCl | 1.25 |
| 10 mmol/l dNTP | 1 |
| 100 μmol/l F1-LP primer | 0.6 |
| 100 μmol/l R3-LP primer | 0.15 |
| 100 μmol/l probe | 0.1 |
| 0.94 U/μl Gene Taq FP*$^2$ | 2 |
| Plasmid sample | 4 |
| Total | 50 |

As the F1-LP primer, the same primer as used in Example 6 was used. A sequence of the R3-LP primer is shown below.

```
R3-LP primer
                                      (SEQ ID NO: 34)
5'-cacaaaatgattctgaattagctgtatcg-3'
```

As the probe for detecting a polymorphism, a mutant-type probe 7 having the following sequence was used. In the sequence, a sequence of the underlined nucleotides is complementary to a sequence of the wild-type codons 12 and the mutant-type codon 13 (gac). The 5' end of the wild-type probe 7 was labeled with a fluorescent substance, TAMRA, and the 3' end of the same was phosphorylated.

```
                                       (SEQ ID NO: 30)
5'-(TAMRA)-cttgcctacgtcacc-P-3'
```

Figure 13:
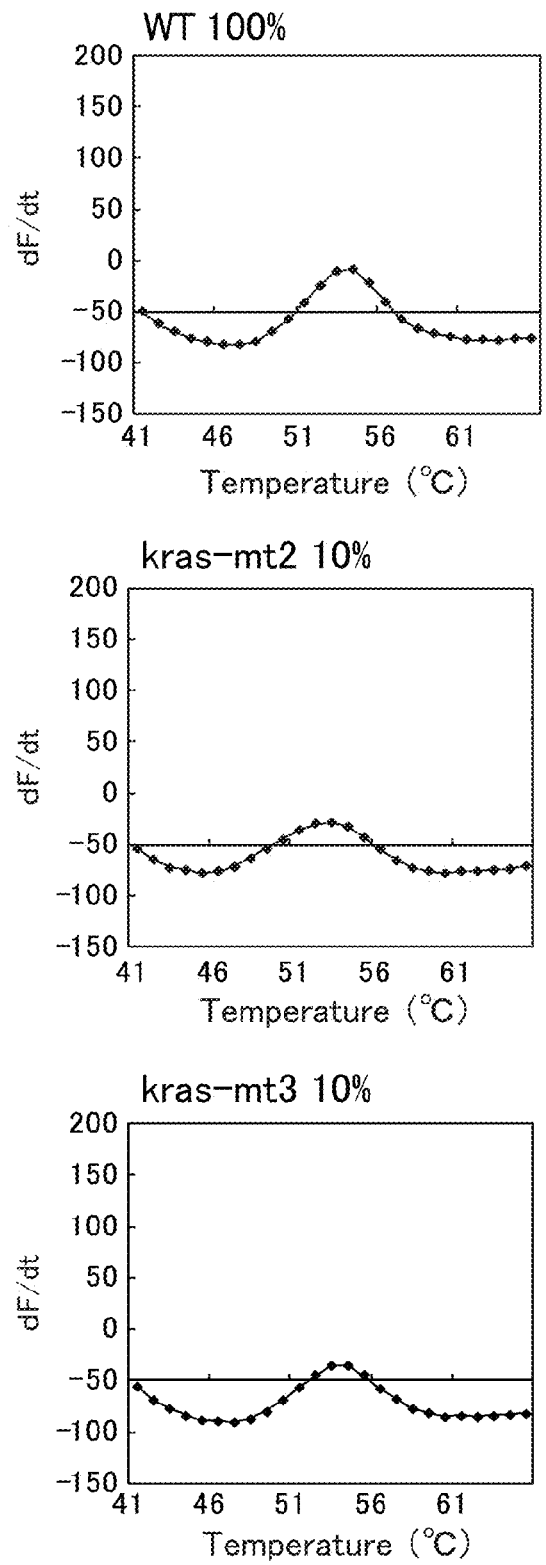
FIG. 13 shows graphs illustrating the results of Tm analysis with respect to the respective reaction solutions, each containing a wild-type plasmid and a mutant-type plasmid in Example 7 of the present invention.
Figure 14:
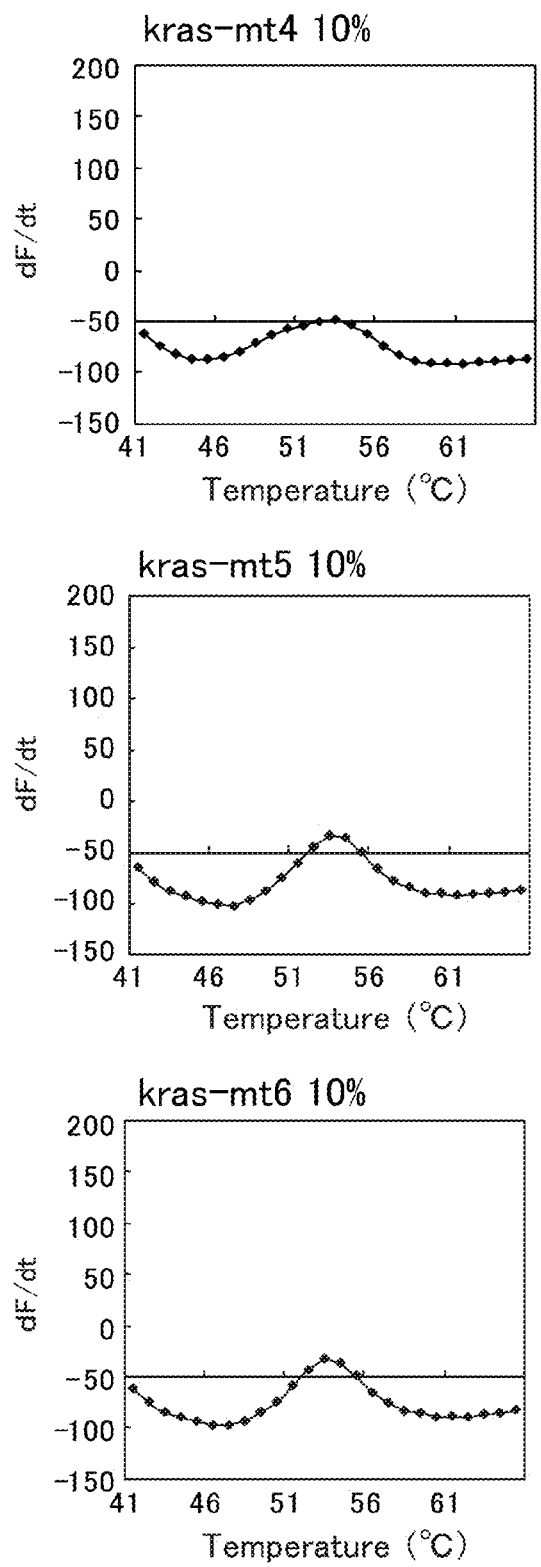
FIG. 14 shows other graphs illustrating the results of Tm analysis with respect to the respective reaction solutions, each containing a wild-type plasmid and a mutant-type plasmid in Example 7 of the present invention.
Figure 15:
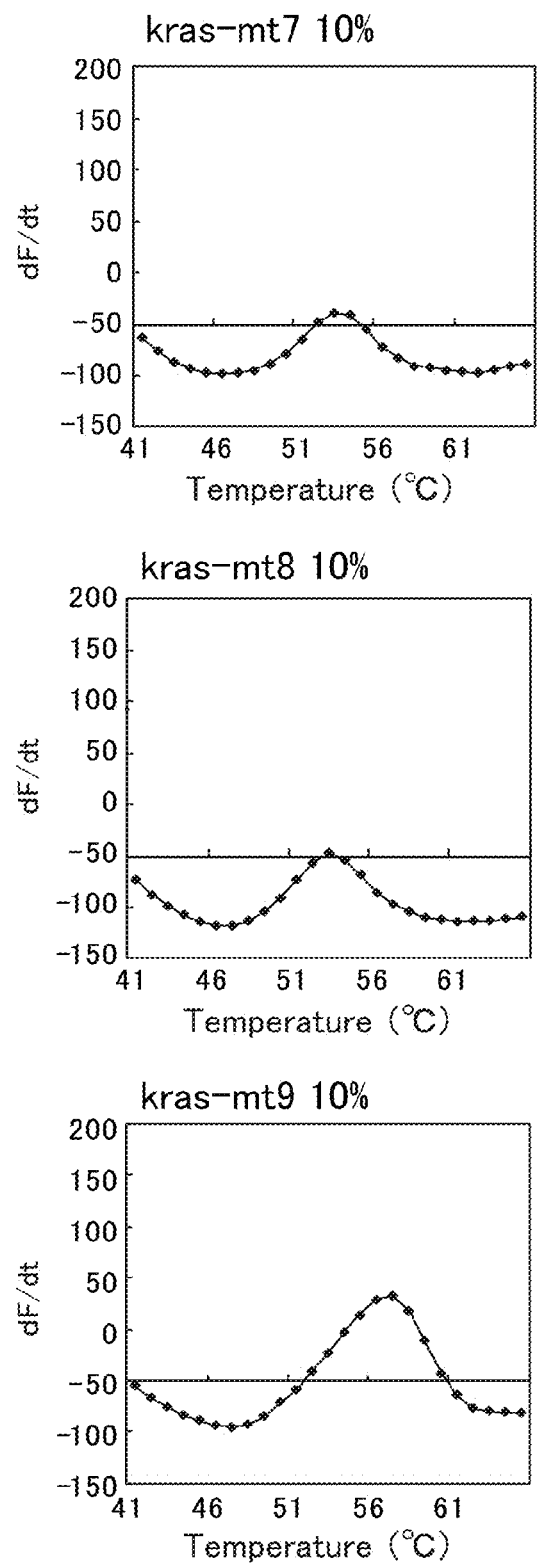
FIG. 15 shows other graphs illustrating the results of Tm analysis with respect to the respective reaction solutions, each containing a wild-type plasmid and a mutant-type plasmid in Example 7 of the present invention.

The results thereof are shown in FIGS. 13 to 15. FIGS. 13 to 15 show graphs showing the Tm analysis results and indicate the change in fluorescence intensity accompanying the temperature rise. FIG. 13 shows the results obtained when the respective plasmid samples were WT 100%, kras-mt 2 10%, and kras-mt 3 10%. FIG. 14 shows the results obtained when the respective plasmid samples were kras-mt 4 10%, kras-mt 5 10%, and kras-mt 6 10%. FIG. 15 shows the results obtained when the respective plasmid samples were kras-mt 7 10%, kras-mt 8 10% and kras-mt 9 10%. In each of FIGS. 13 to 15, the horizontal axis indicates a temperature (° C.) at the time of measurement, and the vertical axis indicates the change in fluorescence intensity, and the unit thereof is "d amount of change in fluorescence intensity/dt" (dF/dt), being a differential value of the amount of change in fluorescence intensity. The Tm value of the formed hybrid between the probe and each of the plasmid was as follows: 54° C. when the plasmid was kras-wt; 53° C. when the plasmid was kras-mt 2; 53.5° C. when the plasmid was kras-mt 3; 53° C. when the plasmid was kras-mt 4; 53° C. when the plasmid was kras-mt 5; 53° C. when the plasmid was kras-mt 6; 53° C. when the plasmid was kras-mt 7; 53° C. when the plasmid was kras-mt 8; and 57° C. when the plasmid was kras-mt 9.

As can be seen from FIGS. 13 to 15, when the plasmid sample was kras-mt 9 10%, a big single peak was observed at about 57° C. When the plasmid sample was any of kras-wt and the other plasmid samples each containing a mutant-type plasmid, only a small peak was observed at about 53° C. to 54° C. As described above, when the plasmid sample was any of the wild-type sample and the samples each containing the wild-type plasmid and any of the mutant-type plasmids 1 to 8, no peak was observed. Therefore, the probe according to the present example could distinguish the mutant-type plasmid 9 10% by the position of the peak and detect it.

INDUSTRIAL APPLICABILITY

As described above, according to the probe of the present invention, a polymorphism in a K-ras gene may be identified easily with high reliability by Tm analysis, for example. Specifically, for example, even in the case where a K-ras gene having a wild-type target polymorphism and a K-ras gene having a mutant-type target polymorphism are present together in a sample, the presence or absence of mutation may be detected easily with high reliability by the Tm analysis using the probe of the present invention. Therefore, the present invention is particularly useful when applied to a sample containing both the wild-type K-ras gene and the mutant-type K-ras gene. As described above, according to the present invention, a polymorphism in a K-ras gene may be identified easily with high reliability, so that, for example, the detection result may be reflected in diagnoses of the above-mentioned diseases and selections of treatment methods for the diseases. Therefore, it can be said that the present invention is very useful in a medical field and the like.

The invention claimed is:

1. An isolated probe selected from the group consisting of oligonucleotides (P1), (P2) and (P3),
   wherein the oligonucleotide (P1) consists of SEQ ID NO: 7,
   the oligonucleotide (P2) consists of an oligonucleotide selected from the group consisting of SEQ ID NO: 8, 9 and 30, and
   the oligonucleotide (P3) consists of SEQ ID NO: 31; and
   wherein each of said oligonucleotides is covalently bonded to a fluorescent dye.

2. The probe according to claim 1, wherein
   the oligonucleotide (P1) is covalently bonded to the fluorescent dye in its 5' end region,
   the oligonucleotide (P2) is covalently bonded to the fluorescent dye in its 5' end region, and
   the oligonucleotide (P3) is covalently bonded to the fluorescent dye in its 5' end region.

3. The probe according to claim 1, wherein
   the oligonucleotide (P1) is covalently bonded to the fluorescent dye at a position of 1st to 4th nucleotides from its 5' end,
   the oligonucleotide (P2) is covalently bonded to the fluorescent dye at a position of 1st to 4th nucleotides from its 5' end, and
   the oligonucleotide (P3) is covalently bonded to the fluorescent dye at a position of 1st to 4th nucleotides from its 5' end.

4. The probe according to claim 1, wherein
   the oligonucleotide (P1) is covalently bonded to the fluorescent dye at 1st nucleotide from its 5' end,
   the oligonucleotide (P2) is covalently bonded to the fluorescent dye at 1st nucleotide from its 5' end, and
   the oligonucleotide (P3) is covalently bonded to the fluorescent dye at 1st nucleotide from its 5' end.

5. The probe according to claim 1, wherein the probe is a probe for use in Tm analysis.

6. The probe according to claim 1, wherein the isolated probe is the oligonucleotide (P2).

7. The probe according to claim 1, wherein the isolated probe is the oligonucleotide (P3).

8. The probe according to claim 1, wherein the fluorescent dye is carboxytetramethylrodamine (TAMRA).

9. A reagent composition which detects a polymorphism in a disease-related gene, comprising the probe according to claim 1.

10. The reagent composition according to claim 9, further comprising primers which amplify a region including a detection target polymorphism in a K-ras gene.

11. The reagent composition according to claim 10, wherein the primers amplify a region comprising nucleotides 220-225 of SEQ ID NO: 1.

12. The reagent composition according to claim 10, wherein the primers comprise a primer pair, said primer pair comprising an oligonucleotide selected from the group consisting of SEQ ID NO: 11, 12 and 32, and an oligonucleotide selected from the group consisting of SEQ ID NO: 13 to 18, 33 and 34.

13. The reagent composition according to claim 10, wherein the primers comprise a primer pair, said primer pair comprising an oligonucleotide consisting of SEQ ID NO: 13, and an oligonucleotides selected from the group consisting of SEQ ID NO: 14, 15, 16 and 17.

14. The reagent composition according to claim 9, further comprising a probe for detecting a polymorphism in a BRAF gene, wherein
   the probe hybridizes to a region comprising nucleotide 229 of SEQ ID NO: 2.

15. The reagent composition according to claim 14, wherein the probe comprises SEQ ID NO: 27 or 36.

16. The reagent composition according to claim 14, further comprising primers to amplify a region comprising a polymorphism in a BRAF gene.

17. The reagent composition according to claim 16, wherein the primers amplify a region comprising nucleotide 229 of SEQ ID NO: 2.

18. The reagent composition according to claim 17, wherein the primers comprise a primer pair, said primer pair comprising an oligonucleotide selected from the group consisting of SEQ ID NO: 20 and 38, and an oligonucleotide selected from the group consisting of SEQ ID NO: 21 and 39.

19. A method of analyzing a polymorphism, the method comprising:
(a) providing a sample comprising a nucleic acid;
(b) contacting the nucleic acid with at least one of the probes of claim 1 to allow said probe to hybridize with the nucleic acid;
(c) changing the temperature to dissociate the hybrid-forming body between the nucleic acid and the probe, and measuring fluctuation of a signal due to the dissociation of said hybrid-forming body;
(d) analyzing said fluctuation of a signal to detect the Tm value of single-stranded nucleic acid in said sample; and
(e) determining based on said Tm value the presence or absence of said polymorphism or the abundance ratio of single-stranded nucleic acid having said polymorphism in single stranded nucleic acid in said sample.

20. The method according to claim 19, wherein at least two probes are used and wherein each is covalently bonded to a different fluorescent dye.

21. The method according to claim 19, wherein prior to, or at the same time as step (b), the nucleic acid is amplified from the sample.

22. The method according to claim 19, wherein the nucleic acid is amplified using primers for amplifying a region comprising nucleotides 220-225 of SEQ ID NO: 1.

23. The method according to claim 22, wherein the primers comprise a primer pair, said primer pair comprising an oligonucleotide selected from the group consisting of SEQ ID NO: 11, 12 and 32, and an oligonucleotide selected from the group consisting of SEQ ID NO: 13 to 18, 33, and 34.

24. The method according to claim 22, wherein the primers comprise a primer pair, said primer pair comprising an oligonucleotide consisting of SEQ ID NO: 13, and an oligonucleotide selected from the group consisting of SEQ ID NO: 14, 15, 16 and 17.

25. The method according to claim 19, further comprising steps of
analyzing a polymorphism in a BRAF gene by further contacting the nucleic acid with a probe comprising a oligonucleotide from the group consisting of SEQ ID NO: 27 and 36 and labelled with fluorescent dye to allow said probe to hybridize with the nucleic acid;
changing the temperature to dissociate the hybrid-forming body between the nucleic acid and said probe, and measuring fluctuation of a signal due to the dissociation of said hybrid-forming body;
analyzing said fluctuation of a signal to detect the Tm value of single-stranded nucleic acid in said sample; and
determining based on said Tm value the presence or absence of said polymorphism or the abundance ratio of single-stranded nucleic acid having said polymorphism in single stranded nucleic acid in said sample.

26. The method according to claim 25, wherein the at least one probe to analyze K-ras and the probe to analyze BRAF are labelled with different fluorescent dyes.

27. The method according to claim 25, wherein prior or at the same time as contacting the nucleic acid with a probe comprising a oligonucleotide from the group consisting of SEQ ID NO: 27 and 36 and labelled with fluorescent dye, the nucleic acid is amplified from the sample using primers that amplifying a region comprising nucleotide 229 of SEQ ID NO: 2.

28. The method according to claim 27, wherein the primers comprise a primer pair, said primer pair comprising an oligonucleotide selected from the group consisting of SEQ ID NO: 20 and 38, and an oligonucleotide selected from the group consisting of SEQ ID NO: 21 and 39.

* * * * *

SEQUENCE LISTING

```
<160> NUMBER OF SEQ ID NOS: 39

<210> SEQ ID NO 1
<211> LENGTH: 500
<212> TYPE: DNA
<213> ORGANISM: Homo sapiens
<220> FEATURE:
<221> NAME/KEY: misc_feature
<222> LOCATION: (220)..(221)
<223> OTHER INFORMATION: n stands for any base

<400> SEQUENCE: 1
acacgtctgc agtcaactgg aattttcatg attgaatttt gtaaggtatt ttgaaataat      60
ttttcatata aaggtgagtt tgtattaaaa ggtactggtg gagtatttga tagtgtatta     120
accttatgtg tgacatgttc taatatagtc acattttcat tattttttatt ataaggcctg    180 ctgaaaatga ctgaatataa acttgtggta gttggagctn ntkrcgtagg caagagtgcc     240
```

```
ttgacgatac agctaattca gaatcatttt gtggacgaat atgatccaac aatagaggta    300
aatcttgttt taatatgcat attactggtg caggaccatt ctttgataca gataaaggtt    360
tctctgacca ttttcatgag tacttattac aagataatta tgctgaaagt taagttatct    420
gaaatgtacc ttgggtttca agttatatgt aaccattaat atgggaactt tactttcctt    480
gggagtatgt cagggtccat                                                500

<210> SEQ ID NO 2
<211> LENGTH: 500
<212> TYPE: DNA
<213> ORGANISM: Homo sapiens

<400> SEQUENCE: 2
tcattgtttt agacatactt attgactcta agaggaaaga tgaagtacta tgttttaaag     60
aatattatat tacagaatta tagaaattag atctcttacc taaactcttc ataatgcttg    120
ctctgatagg aaaatgagat ctactgtttt cctttactta ctacacctca gatatatttc    180
ttcatgaaga cctcacagta aaaataggtg attttggtct agctacagwg aaatctcgat    240
ggagtgggtc ccatcagttt gaacagttgt ctggatccat tttgtggatg gtaagaattg    300
aggctatttt tccactgatt aaattttgg ccctgagatg ctgctgagtt actagaaagt    360
cattgaaggt ctcaactata gtattttcat agttcccagt attcacaaaa atcagtgttc    420
ttatttttta tgtaaataga tttttaact ttttcttta cccttaaaac gaatattttg    480
aaaccagttt cagtgtattt                                                500

<210> SEQ ID NO 3
<211> LENGTH: 23
<212> TYPE: DNA
<213> ORGANISM: Artificial
<220> FEATURE:
<223> OTHER INFORMATION: probe
<220> FEATURE:
<221> NAME/KEY: misc_feature
<222> LOCATION: (10)..(11)
<223> OTHER INFORMATION: n stands for any base

<400> SEQUENCE: 3
cctacgyman nagctccaac tac                                             23

<210> SEQ ID NO 4
<211> LENGTH: 27
<212> TYPE: DNA
<213> ORGANISM: Artificial
<220> FEATURE:
<223> OTHER INFORMATION: probe
<220> FEATURE:
<221> NAME/KEY: misc_feature
<222> LOCATION: (14)..(15)
<223> OTHER INFORMATION: n stands for any base

<400> SEQUENCE: 4
cttgcctacg ymannagctc caactac                                         27

<210> SEQ ID NO 5
<211> LENGTH: 29
<212> TYPE: DNA
<213> ORGANISM: Artificial
<220> FEATURE:
<223> OTHER INFORMATION: probe
<220> FEATURE:
<221> NAME/KEY: misc_feature
<222> LOCATION: (14)..(15)
<223> OTHER INFORMATION: n stands for any base
```

```
<400> SEQUENCE: 5
cttgcctacg ymannagctc caactacca                                     29

<210> SEQ ID NO 6
<211> LENGTH: 27
<212> TYPE: DNA
<213> ORGANISM: Artificial
<220> FEATURE:
<223> OTHER INFORMATION: probe
<220> FEATURE:
<221> NAME/KEY: misc_feature
<222> LOCATION: (16)..(17)
<223> OTHER INFORMATION: n stands for any base

<400> SEQUENCE: 6
ctcttgccta cgymannagc tccaact                                       27

<210> SEQ ID NO 7
<211> LENGTH: 23
<212> TYPE: DNA
<213> ORGANISM: Artificial
<220> FEATURE:
<223> OTHER INFORMATION: probe

<400> SEQUENCE: 7
cctacgccac cagctccaac tac                                           23

<210> SEQ ID NO 8
<211> LENGTH: 27
<212> TYPE: DNA
<213> ORGANISM: Artificial
<220> FEATURE:
<223> OTHER INFORMATION: probe

<400> SEQUENCE: 8
cttgcctacg ccaccagctc caactac                                       27

<210> SEQ ID NO 9
<211> LENGTH: 29
<212> TYPE: DNA
<213> ORGANISM: Artificial
<220> FEATURE:
<223> OTHER INFORMATION: probe

<400> SEQUENCE: 9
cttgcctacg ccaccagctc caactacca                                     29

<210> SEQ ID NO 10
<211> LENGTH: 27
<212> TYPE: DNA
<213> ORGANISM: Artificial
<220> FEATURE:
<223> OTHER INFORMATION: probe

<400> SEQUENCE: 10
ctcttgccta cgccaccagc tccaact                                       27

<210> SEQ ID NO 11
<211> LENGTH: 38
<212> TYPE: DNA
<213> ORGANISM: Artificial
<220> FEATURE:
<223> OTHER INFORMATION: primer

<400> SEQUENCE: 11
```
accttatgtg tgacatgttc taatatagtc acattttc 38

<210> SEQ ID NO 12
<211> LENGTH: 21
<212> TYPE: DNA
<213> ORGANISM: Artificial
<220> FEATURE:
<223> OTHER INFORMATION: primer

<400> SEQUENCE: 12
aaggcctgct gaaaatgact g 21

<210> SEQ ID NO 13
<211> LENGTH: 17
<212> TYPE: DNA
<213> ORGANISM: Artificial
<220> FEATURE:
<223> OTHER INFORMATION: primer

<400> SEQUENCE: 13
ctcttgccta cgccacc 17

<210> SEQ ID NO 14
<211> LENGTH: 19
<212> TYPE: DNA
<213> ORGANISM: Artificial
<220> FEATURE:
<223> OTHER INFORMATION: primer

<400> SEQUENCE: 14
cactcttgcc tacgccacd 19

<210> SEQ ID NO 15
<211> LENGTH: 19
<212> TYPE: DNA
<213> ORGANISM: Artificial
<220> FEATURE:
<223> OTHER INFORMATION: primer

<400> SEQUENCE: 15
gcactcttgc ctacgccad 19

<210> SEQ ID NO 16
<211> LENGTH: 21
<212> TYPE: DNA
<213> ORGANISM: Artificial
<220> FEATURE:
<223> OTHER INFORMATION: primer

<400> SEQUENCE: 16
caaggcactc ttgcctacgc a 21

<210> SEQ ID NO 17
<211> LENGTH: 21
<212> TYPE: DNA
<213> ORGANISM: Artificial
<220> FEATURE:
<223> OTHER INFORMATION: primer

<400> SEQUENCE: 17
tcaaggcact cttgcctacg t 21

<210> SEQ ID NO 18
<211> LENGTH: 22
<212> TYPE: DNA
<213> ORGANISM: Artificial

```
<220> FEATURE:
<223> OTHER INFORMATION: primer

<400> SEQUENCE: 18
ggtcctgcac cagtaatatg ca                                          22

<210> SEQ ID NO 19
<211> LENGTH: 19
<212> TYPE: DNA
<213> ORGANISM: Artificial
<220> FEATURE:
<223> OTHER INFORMATION: probe

<400> SEQUENCE: 19
ctagctacag wgaaatctc                                              19

<210> SEQ ID NO 20
<211> LENGTH: 27
<212> TYPE: DNA
<213> ORGANISM: Artificial
<220> FEATURE:
<223> OTHER INFORMATION: primer

<400> SEQUENCE: 20
cctttactta ctacacctca gatatat                                     27

<210> SEQ ID NO 21
<211> LENGTH: 23
<212> TYPE: DNA
<213> ORGANISM: Artificial
<220> FEATURE:
<223> OTHER INFORMATION: primer

<400> SEQUENCE: 21
acaactgttc aaactgatgg gac                                         23

<210> SEQ ID NO 22
<211> LENGTH: 50
<212> TYPE: DNA
<213> ORGANISM: Artificial
<220> FEATURE:
<223> OTHER INFORMATION: oligonucleotide

<400> SEQUENCE: 22
aacttgtggt agttggagct ggtggcgtag gcaagagtgc cttgacgata            50

<210> SEQ ID NO 23
<211> LENGTH: 50
<212> TYPE: DNA
<213> ORGANISM: Artificial
<220> FEATURE:
<223> OTHER INFORMATION: oligonucleotide

<400> SEQUENCE: 23
aacttgtggt agttggagct tgtggcgtag gcaagagtgc cttgacgata            50

<210> SEQ ID NO 24
<211> LENGTH: 50
<212> TYPE: DNA
<213> ORGANISM: Artificial
<220> FEATURE:
<223> OTHER INFORMATION: oligonucleotide

<400> SEQUENCE: 24
aacttgtggt agttggagct gatggcgtag gcaagagtgc cttgacgata            50
```

```
<210> SEQ ID NO 25
<211> LENGTH: 50
<212> TYPE: DNA
<213> ORGANISM: Artificial
<220> FEATURE:
<223> OTHER INFORMATION: oligonucleotide

<400> SEQUENCE: 25
aacttgtggt agttggagct ggtgacgtag gcaagagtgc cttgacgata            50

<210> SEQ ID NO 26
<211> LENGTH: 50
<212> TYPE: DNA
<213> ORGANISM: Artificial
<220> FEATURE:
<223> OTHER INFORMATION: oligonucleotide

<400> SEQUENCE: 26
aacttgtggt agttggagct aatggcgtag gcaagagtgc cttgacgata            50

<210> SEQ ID NO 27
<211> LENGTH: 19
<212> TYPE: DNA
<213> ORGANISM: Artificial
<220> FEATURE:
<223> OTHER INFORMATION: probe

<400> SEQUENCE: 27
ctagctacag agaaatctc                                              19

<210> SEQ ID NO 28
<211> LENGTH: 19
<212> TYPE: DNA
<213> ORGANISM: Artificial
<220> FEATURE:
<223> OTHER INFORMATION: probe

<400> SEQUENCE: 28
ctagctacag tgaaatctc                                              19

<210> SEQ ID NO 29
<211> LENGTH: 15
<212> TYPE: DNA
<213> ORGANISM: Artificial
<220> FEATURE:
<223> OTHER INFORMATION: probe
<220> FEATURE:
<221> NAME/KEY: misc_feature
<222> LOCATION: (14)..(15)
<223> OTHER INFORMATION: n stands for any base

<400> SEQUENCE: 29
cttgcctacg ymann                                                  15

<210> SEQ ID NO 30
<211> LENGTH: 15
<212> TYPE: DNA
<213> ORGANISM: Artificial
<220> FEATURE:
<223> OTHER INFORMATION: probe

<400> SEQUENCE: 30
cttgcctacg tcacc                                                  15

<210> SEQ ID NO 31
<211> LENGTH: 39
```

```
<212> TYPE: DNA
<213> ORGANISM: Artificial
<220> FEATURE:
<223> OTHER INFORMATION: probe

<400> SEQUENCE: 31
ctcttgccta cgccaccagc tccaacttgc tggctacgc                    39

<210> SEQ ID NO 32
<211> LENGTH: 26
<212> TYPE: DNA
<213> ORGANISM: Artificial
<220> FEATURE:
<223> OTHER INFORMATION: primer

<400> SEQUENCE: 32
ggtactggtg gagtatttga tagtgt                                  26

<210> SEQ ID NO 33
<211> LENGTH: 26
<212> TYPE: DNA
<213> ORGANISM: Artificial
<220> FEATURE:
<223> OTHER INFORMATION: primer

<400> SEQUENCE: 33
gaattagctg tatcgtmaag gcactc                                  26

<210> SEQ ID NO 34
<211> LENGTH: 29
<212> TYPE: DNA
<213> ORGANISM: Artificial
<220> FEATURE:
<223> OTHER INFORMATION: primer

<400> SEQUENCE: 34
cacaaaatga ttctgaatta gctgtatcg                               29

<210> SEQ ID NO 35
<211> LENGTH: 16
<212> TYPE: DNA
<213> ORGANISM: Artificial
<220> FEATURE:
<223> OTHER INFORMATION: probe

<400> SEQUENCE: 35
gctacagwga aatctc                                             16

<210> SEQ ID NO 36
<211> LENGTH: 16
<212> TYPE: DNA
<213> ORGANISM: Artificial
<220> FEATURE:
<223> OTHER INFORMATION: probe

<400> SEQUENCE: 36
gctacagaga aatctc                                             16

<210> SEQ ID NO 37
<211> LENGTH: 16
<212> TYPE: DNA
<213> ORGANISM: Artificial
<220> FEATURE:
<223> OTHER INFORMATION: probe

<400> SEQUENCE: 37
```

```
gctacagtga aatctc                                                    16

<210> SEQ ID NO 38
<211> LENGTH: 30
<212> TYPE: DNA
<213> ORGANISM: Artificial
<220> FEATURE:
<223> OTHER INFORMATION: primer

<400> SEQUENCE: 38
tgcttgctct gataggaaaa tgagatctac                                     30

<210> SEQ ID NO 39
<211> LENGTH: 22
<212> TYPE: DNA
<213> ORGANISM: Artificial
<220> FEATURE:
<223> OTHER INFORMATION: primer

<400> SEQUENCE: 39
aaactgatgg gacccactcc at                                             22
```